US006986894B2

(12) United States Patent
O'Brien et al.

(10) Patent No.: US 6,986,894 B2
(45) Date of Patent: Jan. 17, 2006

(54) METHODS FOR THE TREATMENT OF COAGULATION DISORDERS WITH LIPOPROTEIN ASSOCIATED COAGULATION INHIBITOR (LACI)

(75) Inventors: Donogh P. O'Brien, Harrow (GB); Gordon A. Vehar, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 45 days.

(21) Appl. No.: 09/924,857

(22) Filed: Aug. 8, 2001

(65) Prior Publication Data

US 2003/0206904 A1 Nov. 6, 2003

Related U.S. Application Data

(63) Continuation of application No. 08/476,837, filed on Jun. 7, 1995, now Pat. No. 6,274,142, which is a continuation of application No. 08/260,662, filed on Jun. 16, 1994, now Pat. No. 5,589,173, which is a continuation of application No. 08/076,280, filed on Jun. 11, 1993, now abandoned, which is a continuation of application No. 07/887,575, filed on May 18, 1992, now abandoned, which is a continuation-in-part of application No. 07/237,595, filed on Aug. 25, 1988, now abandoned, which is a continuation-in-part of application No. 07/209,665, filed on Jun. 21, 1988, now abandoned, which is a continuation-in-part of application No. 07/110,255, filed on Oct. 20, 1987, now abandoned, which is a continuation-in-part of application No. 06/926,977, filed on Nov. 4, 1986, now abandoned.

(51) Int. Cl.
*A61K 38/17* (2006.01)
*C07K 14/745* (2006.01)

(52) U.S. Cl. .......................... 424/278.1; 514/2; 514/8; 530/350

(58) Field of Classification Search ............. 424/278.1; 514/218; 530/350
See application file for complete search history.

(56) References Cited

U.S. PATENT DOCUMENTS

| | | | |
|---|---|---|---|
| 4,416,812 | A | 11/1983 | Becker |
| 4,470,968 | A | 9/1984 | Mitra et al. |
| 4,473,553 | A | 9/1984 | Zuffi et al. |
| 4,966,852 | A | 10/1990 | Wun et al. |
| 5,017,556 | A | 5/1991 | O'Brien et al. |
| 5,106,833 | A * | 4/1992 | Broze et al. |
| 5,110,730 | A | 5/1992 | Edgington et al. |
| 5,589,173 | A | 12/1996 | O'Brien et al. |

FOREIGN PATENT DOCUMENTS

EP 266993 5/1988

OTHER PUBLICATIONS

Bach et al. *Abstracts of the 59th Scientific Sessions* (oral presentation, Annual Convention of the American Heart Assn.) (Nov. 19, 1986).
Bach et al., "Factor VII Binding to Tissue Factor in Reconstituted Phospholipid Vesicles: Induction of Cooperativity by Phosphatidylserine" *Biochemistry* 25(14): 4007-4020 (1986).
Bach et al., "Purification and Characterization of Bovine Tissue Factor" *Journal of Biological Chemistry* 256(16): 8324-8331 (1981).
Baldus et al., "Successful recanalization of experimentally occluded coronary arteries in anesthetised dogs and recombinant single-chain tissue-type plasminogen activator (sct-PA)" *Fibrinolysis* 1(1):23-28 (1987).
Beck et al. *Hematology*, MIT Press pps. 381-382 & 436-437 (1981).
Bjorklid et al., "Purification and Some Properties of the Protein Component of Tissue Thromboplastin from Human Brain" *Biochemical Journal* 165(1):89-96 (1977).
Bjorklid et al., "The Protein Component of Human Brain Thromboplastin" *Biochemical and Biophysical Research Communications* 55(3):969-976 (1973).
Blakeslee et al., "Scientists find Long-Sought Key to How Blood Clots" *New York Times* (Jul. 7, 1987).
Bom et al., "Application of Factor VII-Sepharose Affinity Chromatography in the Purification of Human Tissue Factor Apoprotein" *Thrombosis Research* 42:635-643 (1986).
Brommer et al., "Survival of fibrinogen degradation products in the circulation after thrombolytic therapy for acute myocardial infarction" *Fibrolysis* 1(3):149-153 (1987).
Broze et al., "Isolation of the Tissue Factor Inhibitor Produced by HepG2 Hepatoma Cells" *Proc. Natl. Acad. Sci. USA* 84:1886-1890 (Apr. 1987).
Broze, Jr. et al., "The Lipoprotein-Associated Coagulation Inhibitor That Inhibits the Factor VII-Tissue Factor Complex Also Inhibits Factor Xa: Insight Into Its Possible Mechanism of Action" *Blood* 71(2):335-343 (Feb. 1988).
Broze, Jr., et al., "Purification of Human Brain Tissue Factor" *Journal of Biological Chemistry* 260(20):10917-10920 (1985).
Callas et al., "Comparative Pharmacology of Site Directed Antithrombin Agents. Implication in Drug Development" *Thrombosis and Haemostasis* 74(1):473-481 (1995).

(Continued)

*Primary Examiner*—Phillip Gambel
(74) *Attorney, Agent, or Firm*—Elinor K. Shin

(57) ABSTRACT

The present invention related to a method and therapeutic composition for the treatment of coagulation disorders comprising administration of a lipoprotein associated coagulation inhibitor.

7 Claims, 9 Drawing Sheets

OTHER PUBLICATIONS

Carlsen et al., "Intravenous Injections of Tissue Thromboplastin and Phospholipase C in Sheep" *Thrombosis Haemostasis* 48(3):315-319 (1982).

Carson et al., "An inhibitory monoclonal antibody against human tissue factor" *Blood* 70(2):490-493 (1987).

Carson et al., "Lipid activation of coagulation factor III apoprotein (tissue factor)—reconstitution of the protein-membrane complex" *Chemical Abstracts* 94(244):13337f (1981).

Carson et al., "Monoclonal Antibodies Aginst Bovine Tissue Factor, Which Block Interaction with Factor VIIa" *Blood* 66(1):152-156 (1985).

Carson et al., "Plasma High Density Lipoproteins Inhibit the Activation of Coagulation Factor X by Factor VIIa and Tissue Factor" *FEBS Letters* 132(1):37-40 (1981).

Carson et al., "Tissue Factor Gene Localized to Human Chromosome 1 (1pter-1p21)" *Science* 229:991-993 (1985).

Carson, S.D., "Tissue Factor-Initiated Blood Coagulation" *Progress in Clinical Pathology*, Stefanini et al., Grune & Stratton vol. 9:1-14 (1984).

Collen et al., "Thrombolytic Therapy" *Annu. Rev. Med.* 39:405-423 (Apr. 1988).

Dennis and Lazarus, "Kunitz Domain Inhibitors of Tissue Factor-Factor VIIa; I. Potent Inhibitors Selected from Libraries by Phage Display" *Journal of Biological Chemistry* 269(35):22129-22136 (1994).

*Dorland's Illustrated Medical Dictionary*, 26th edition, W. B. Saunders Company pps. 281-282, 1071 (1981).

Edgington et al., "Molecular Cloning of Human Tissue Factor cDNA" *Thrombosis and Haemostasis* (Abstract No. 941) 58(1):258 (Jan. 1987).

Esnouf, "Extrinsic Activation of Prothrombin" *Human Blood Coagulation, Haemostasis and Thrombosis* pps. 55-65 (1976).

Ewan et al., "Production and Characterization of a Monoclonal Antibody (A1-3) That Binds Selectively to Activated Monocytes and Inhibits Monocyte Procoagulant Activity" *J. Immunol.* 136(7):2408-2415 (1986).

Falk, "Plaque Rupture with Severe Pre-existing Stenosis Precipitating Coronary Thrombosis" *Br. Heart J.* 50:127-134 (1983).

Fisher et al., "Cloning and Expression of Human Tissue Factor cDNA" *Thrombosis Research* 48(1):89-99 (1987).

Freyssinet et al., "Coextraction of Thrombomodulin and Tissue Factor from Human Placenta: Effects of Concanavalin A and Phospholid Environment on Activity" *Thrombosis and Haemostasis* 55(1):112-118 (1986).

Giercksky et al., "The Effect of Intravenous Injection of Purified Human Tissue Thromboplastin in Rats" *Scand. J. Haematol.* 16(4):300-310 (Apr. 1976).

Gitel et al., "The Antithrombotic Effects of Warfarin and Heparin Following Infusions of Tissue Thromboplastin in Rabbits: Clinical Implications" *J. of Laboratory Clinical Medicine* 94(3):481-488 (1979).

Gollub et al., "Thromboplastinase-an Experimental Antithrombotic" *Thromb. Diath. Haemorh.* 7:470-479 (1962).

Gonmori et al., "The Role of Tissue Thromboplastin in the Development of DIC Accompanying Neoplastic Diseases" *Biblio. Haematol.* 49:23-39 (1983).

Guha et al., "Affinity purification of human tissue factor: Interaction of factor VII and tissue factor in detergent micelles" *Proc. Natl. Acad. Sci. USA* 83:299-302 (1986).

Harker, "Role of Platelets and Thrombosis in Mechanisms of Acute Occlusion and Restenosis After Angioplasty" *The American Journal of Cardiology* 60:20B-28B (Jul. 1987).

Haskel et al., "Prevention of Arterial Reocclusion After Thrombolysis With Recombinant Lipoprotein-Associated Coagulation Inhibitor" *Circulation* 84(2):821-827 (1991).

Haskel et al., "Prevention of Reoccluding Platelet-Rich Thrombi in Canine Femoral Arteries With a Novel Peptide Antagonist of Platelet Glycoprotein IIb/IIIa Receptors" *Circulation* 80(6):1775-1782 (1989).

Jang et al., "Antithrombotic Effect of a Monoclonal Antibody Against Tissue Factor in a Rabbit Model of Platelet-Mediated Arterial Thrombosis" *Arteriosclerosis and Thrombosis* 12(8):948-954 (Aug. 1992).

Johns et al., "Prevention of Coronary Artery Reocclusion and Reduction in Late Coronary Artery Stenosis After Thrombolytic Therapy in Patients With Acute Myocardial Infarction" *Circulation* 78(3):546-556 (1988).

Kelley et al., "Analysis of the Factor VIIa Binding Site on Human Tissue Factor: Effects of Tissue Factor Mutations on the Kinetics and Thermodynamics of Binding" *Biochemistry* 34(33):10383-10392 (1995).

Kittler et al., "Identification of a cDNA Clone for Bovine Tissue Factor" *76th Ann. Mtg. of the American Society of Biol. Chemists, Wash., D.C., Fed. Proc.* (Abstract 927) 45(6):1639 (Jun. 1986).

Konigsberg et al., "Molecular Cloning of the cDNA for Human Tissue Factor" *Cell* 52:639-640 (1988).

Kurosawa et al., "Urinary Procoagulant Behaves as Tissue Factor by Promoting Factor VIIa-Catalyzed Activation of Factor X" *Thrombosis Research* 33:595-606 (1984).

Lewis et al., "Effects of intrvaneous tissue thomboplastin in dogs: Development of an anticoagulant" *J. of Laboratory Clinical Medicine* 60(2):261-273 (1962).

Light, A., "Protein Solubility, Protein Modifications and Protein Folding" *Biotechniques* 3(4):298-306 (1985).

Lindahl, "Tissue Factor Pathway Inhibitor: A Potent Inhibitor in In-Vitro Coagulation and In-Vivo Thrombus Formation" *Current Opinion in Lipidology* 5:434-439 (1994).

Lyberg, "Clinical Significance of Increased Thromboplastin Activity on the Monocyte Surface—A Brief Review" *Haemostasis* 14(5):430-439 (1984).

Morrissey et al., "Differential Expression and Subcellular Localization of Tissue Factor in Constitutive Versus an Inducible Cell Type" *Thrombosis and Haemostasis* (Abstract No. 940) 58(1):258 (1987).

Morrissey et al., "Molecular Cloning of the cDNA for Human Tissue Factor" *Fed. of Amer. Society for Exp. Biol.* (71st Annual Mtg. Mar. 29, 1987-Apr. 2, 1987, Abstract #2338) 46(3):716 (Mar. 1, 1987).

Morrissey et al., "Molecular Cloning of the cDNA for Tissue Factor, the Cellular Receptor for the Initiation of the Coagulation Protease Cascade" *Cell* 50(1):129-135 (1987).

Morrissey et al., "Properties of Tissue Factor Purified from Human Brain and Placenta" *Abstracts of the 59th Scientific Sessions* (Annual Convention of the American Heart Assn., Abstract #1632) (Nov. 1986).

Morrissey et al., "Resolution of Monomeric and Heterodimeric Forms of Tissue Factor, the High Affinity Cellular Receptor for Factor VII" *Thrombosis Research* 50:481-493 (1988).

Nemerson et al., "The role of lipids in the tissue factor pathway of blood coagulation" *Chemical Abstracts* 84 (133467P):314 (1976).

Nemerson et al., "Tissue Factor Revisited" *Progress in Hemostasis and Thrombosis* 6:237-260 (1982).

Nemerson, "Characteristics and Lipid Requirements of Coagulant Proteins Extracted from Lung and Brain: the Specificity of the Protein Component of Tissue Factor" *J. Clin. Invest.* 48:322-330 (1969).

Nemerson, "The Phospholid Requirement of Tissue Factor in Blood Coagulation" *J. Clin. Invest.* 47:72-80 (1968).

Ngo et al., "Computational Complexity, Protein Structure Prediction, and the Levinthal Paradox" *The Protein Folding Problem and Tertiary Structure Prediction*, Merz & Le Grand, Boston:Birkhauser pps. 491-495 (1994).

Niemetz, J., "Coagulant Activity of Leukocytes" *J. Clin. Invest.* 51:307-313 (1972).

Osterud et al., "Activation pathways of the coagulation system in normal haemostasis" *Scand. J. Haematol.* 32:337-345 (1984).

Osterud, B., "The Interaction of Human blood Coagulation Factor VII and Tissue Factor: The Effect of Anti Factor VII, anti Tissue Factor an Diisopropylfluorophosphate" *Biochem. & Biophys. Res. Comm.* 88(1):59-67 (1979).

Pawashe et al., "A Monoclonal Antibody Against Rabbit Tissue Factor Inhibits Thrombus Formation in Stenotic Injured Rabbit Carotid Arteries" *Circ. Res.* 74(1):56-63 (Jan. 1994).

Pepe et al., "Functional site on Human Tissue Factor" *FASEB J.* (Abstract No. 552) 2(4):A391 (May 5, 1988).

Pitlick et al., "Binding of the Protein Component of Tissue Factor to Phospholids" *Biochemistry* 9(26):5105-5113 (1970).

Pitlick et al., "Concanavalin A Inhibits Tissue Factor Coagulant Activity" *J. Clin. Invest.* 55:175-179 (1975).

Rao et al., "Affinity Purification of Human Brain Tissue Factor Utilizing Factor VII Bound Immobilized Anti-factor VII 1,2" *Analytical Biochemistry* 165:365-70 (1987).

Ross, Russell, "The Pathogenesis of Atherosclerosis—An Update" *N. England Jour. of Medicine* 314(8):488-500 (1986).

Scarpati et al., "Human Tissue Factor: cDNA Cloning, Primary Structure, and Chromosome Localization" (Paper 1846, Amer. Society for Exp. Biol. 78th Annual Mtg. Jun. 7, 1987-Jun. 11, 1987) 46(6):2242 (abs) (May 1, 1987).

Scarpati et al., "Human Tissue Factor: cDNA Sequence and Chromosome Localization of the Gene" *Biochemistry* 26 (17):5234-5238 (1987).

Schneider, "The Active Principle of Placental Toxin: Thromboplastin; Its Inactivator in Blood: Antithromboplastin" *Am. J. Physiol.* 149:123-127 (1946).

Sojar et al., "A Chemical Method for the Deglycosylation of Proteins" *Archives of Biochemistry & Biophysics* 259(1):52-57 (1987).

Spicer et al., "Isolation of cDNA clones coding for human tissue factor: Primary structure of the protein and cDNA" *Proc. Natl. Acad. Sci. USA* 84(15):5148-5152 (1987).

Stirling, "Warfarin-induced Changes in Procoagulant and Anticoagulant Proteins" *Blood Coagulation and Fibrinolysis* 6:361-373 (1995).

Tanaka et al., "Purification of Glycosylated Apoprotein of Tissue Factor from Human Brain and Inhibition of Its Procoagulant Activity by a Specific Antibody" *Chemical Abstracts* (Abstract No. 49211z) 104:366 (1986).

Tanaka et al., "Purification of Glycosylated Apoprotein of Tissue Factor from Human Brain and Inhibition of its Procoagulant Activity by a Specific Antibody" *Thrombosis Research* 40:745-756 (1985).

Thomas, "Studies on the Intravascular Thromboplastic Effect of Tissue Suspensions in Mice" *Bull. Johns Hopkins Hospital* 81:26-42 (1947).

Van Den Besselaar et al., "Tissue Factor-Induced Coagulation Can Be Inhibited by Aprotinin (Trasylol)" *Thrombosis and Haemostasis* 69:298-299 (1993).

Vehar, "Recombinant DNA Technology and Its Impact on Our Understanding of Factor VIII" *Factor VIII/von Willebrand Factor: Biological and Clinical Advances, Proc. Bari Int. Conf.*, S Wichpig edition, Italy pps. 267-274 (1986).

Wilcox et al., "Localization of Tissue Factor in the Normal Vessel Wall and in the Atherosclerotic Plaque" *Proc. Natl. Acad. Sci. USA* 86:2839-2843 (Apr. 1989).

Zacharski et al., [20~, "Reduced Tissue Factor (Thromboplastin) Activity in von Willebrand's Disease" *American J. of Medicine* 57:102-107 (1974).

Zuniga, M. C. et al., "Expression and Function of Transplantation Antigens with Altered or Deleted Cytoplasmic Domains" *Cell* 34:535-544 (1983).

* cited by examiner

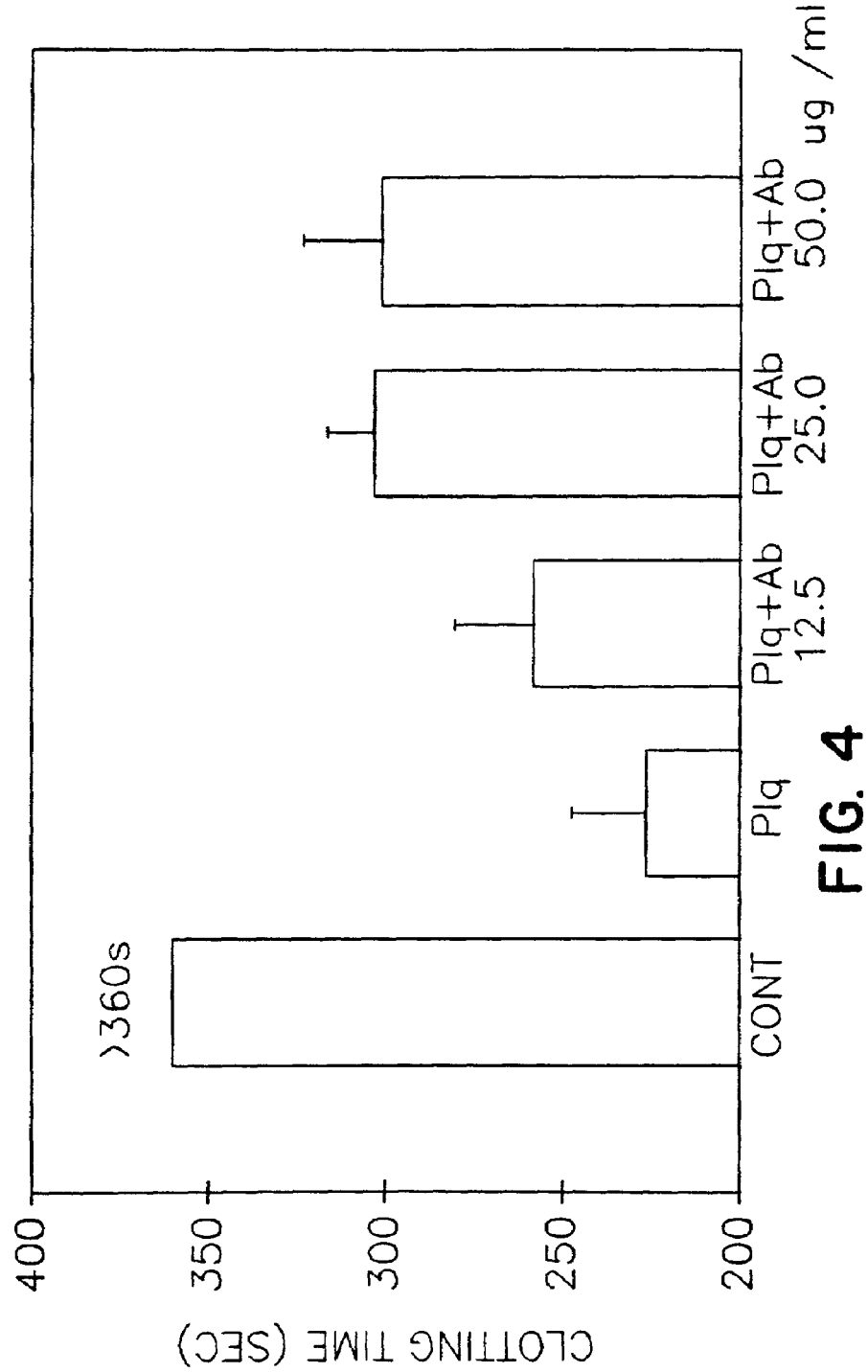

METHODS FOR THE TREATMENT OF COAGULATION DISORDERS WITH LIPOPROTEIN ASSOCIATED COAGULATION INHIBITOR (LACI)

This application is a continuation of application Ser. No 08/476,837 filed on 7 Jun. 1995, now U.S. Pat. No. 6,274,142, which is a continuation of Ser. No. 08/260,662 filed on 16 Jun. 1994, now U.S. Pat. No. 5,589,173, which is a continuation of Ser. No. 08/076,280 filed on 11 June 1993 now abandoned, which is a continuation of Ser. No. 07/887,575 filed on 18 May 1992, now abandoned, which is a continuation in part of Ser. No. 07/237,595 filed on 25 Aug. 1988, now abandoned, which is a continuation in part of Ser. No. 07/209,665 filed on 21 Jun. 1988, now abandoned, which is a continuation in part of Ser. No. 07/110,255 filed on 20 Oct. 1987, now abandoned, which is a continuation in part of Ser. No. 06/926,977 filed 4 Nov. 1986, now abandoned, which applications are incorporated herein by reference.

BACKGROUND OF THE INVENTION

This invention relates to the treatment of myocardial infarction and more particularly to a therapy capable of preventing the reocclusion of a coronary artery which often accompanies the use of thrombolytic agents in the treatment of myocardial infarction. This invention also relates to the use of tissue factor protein inhibitors to prevent reocclusion of a coronary artery.

The initiating event of many myocardial infarctions (heart attacks) is the hemorrhage into an atherosclerotic plaque. Such hemorrhage often results in the formation of a thrombus (or blood clot) in the coronary artery which supplies the infarct zone (i.e., an area of necrosis which results from an obstruction of blood circulation). This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

The primary goal of current treatment for myocardial infarction involves the rapid dissolution of the occluding thrombus and the restoration of blood flow ("reperfusion"). A successful therapy must be capable of eliminating the fibrin-platelet clot in a manner which prevents its reformation after the cessation of therapy. If the fibrin-platelet clot is able to reform, then the affected artery may become reoccluded.

The formation of fibrin-platelet clots in other parts of the circulatory system may be partially prevented through the use of anti-coagulants (such as heparin). Unfortunately, heparin has not been found to be universally effective in preventing reocclusion in myocardial infarction victims in which the degree of blood vessel occlusion (the degree of "stenosis") is greater than or equal to 70%, particularly in those patients with severe residual coronary stenosis.

If an individual has formed a fibrin-platelet clot, the clot may be dissolved through the use of thrombolytic agents. A thrombolytic agent is a medicament capable of lysing the fibrin-platelet thrombus, and thereby permitting blood to again flow through the affected blood vessel. Such agents include streptokinase, prourokinase, urokinase, and tissue-type plasminogen activator (Ganz, W. et al., J. Amer. Coll. Cardiol. 1:1247–1253 [1983]; Rentrop, K. P. et al., Amer. J. Cardiol. 54:29E-31E [1984]; Gold, H. K. et al., Amer. J. Cardiol. 53:122C–125C [1984]). [1986]). Increased t-PA dosages have not been found to decrease the tendency for coronary artery reocclusion. Significantly, the possibility of thrombin clot reformation is closely related to the degree of residual coronary stenosis (i.e., the extent of blood vessel blockage). Thus, reocclusion is more probable in individuals in which high grade stenosis (i.e., greater than 70% quantitative stenosis or greater than 80% non-quantitative stenosis) has occurred. The reocclusion of blood vessels has been found to be inhibited by continued infusion of t-PA (Gold, H. K. et al., Circulation 73:347–352 [1986]). This is a less than optimal treatment in that once infusion is stopped, the vessel reoccludes.

The general mechanism of blood clot formation is reviewed by Ganong, W. F. (In: Review of Medical Physiology, 9th ed., Lange, Los Altos, Calif., pp 411–414 [1979]). Blood coagulation performs two functions; the production of thrombin which induces platelet aggregation and the formation of fibrin which renders the platelet plug stable. A number of discrete proenzymes and procofactors, referred to as "coagulation factors", participate in the coagulation process. The process consists of several stages and ends with fibrin formation. Fibrinogen is converted to fibrin by the action of thrombin. Thrombin is formed by the proteolytic cleavage of a proenzyme, prothrombin. This proteolysis is effected by activated factor X (referred to as factor $X_a$) which binds to the surface of activated platelets and in the presence of Va and ionic calcium cleaves prothrombin.

Activation of factor X may occur by either of two separate pathways, the extrinsic or the intrinsic. The intrinsic cascade consists of a series of reactions wherein a protein precursor is cleaved to form an active protease. At each step, the newly formed protease will catalyze the activation of another protease at the subsequent step of the cascade. A deficiency of any of the proteins in the pathway blocks the activation process at that step, thereby preventing clot formation and typically gives rise to a tendency to hemorrhage. Deficiencies of factor VIII or factor IX, for example, cause the severe bleeding syndromes haemophilia A and B, respectively. In the extrinsic pathway of blood coagulation, tissue factor, also referred to as tissue thromboplastin, is released from damaged cells and facilitates factor X in the presence of factor VII and calcium. Although activation of factor X was originally believed to be the only reaction catalyzed by tissue factor and factor VII, it is now known that an amplification loop exists between factor X, factor VII, and factor IX (Osterud, B., and S. I. Rapaport, Proc. Natl. Acad. Sci. USA 74:5260–5264, 1977; Zur, M. et al., Blood 52: 198, 1978). Each of the serine proteases in this scheme is capable of converting by proteolysis the other two into the activated form, thereby amplifying the signal at this stage in the coagulation process (FIG. 2). It is now believed that the extrinsic pathway may in fact be the major physiological pathway of normal blood coagulation (Haemostasis 13:150–155 1983). Since tissue factor is not normally found in the blood, the system does not continuously clot; the trigger for coagulation would therefore be the release or exposure of tissue factor from damaged tissue, e.g. atherosclerotic plaque.

Tissue factor is an integral membrane glycoprotein which, as discussed above, can trigger blood coagulation via the extrinsic pathway. Bach, R. et al., J. Biol Chem. 256(16), 8324–8331 (1981). Tissue factor consists of a protein component (previously referred to as tissue factor apoprotein-III) and a phospholipid. Osterud, B. and Rapaport, S. I., PNAS 74, 5260–5264 (1977). The complex has been found on the membranes of monocytes and different cells of the blood vessel wall. Osterud, B., Scand. J. Haematol. 32, 337–345

(1984). Tissue factor from various organs and species has been reported to have a relative molecular mass of 42,000 to 53,000. Human tissue thromboplastin has been described as consisting of a tissue factor protein inserted into phospholipid bilayer in an optimal ratio of tissue factor protein: phospholipid of approximately 1:80. Lyberg, T. and Prydz, H., Nouv. Rev. Fr. Hematol. 25(5), 291–293 (1983). Purification of tissue factor has been reported from various tissues such as,: human brain (Guha, A. et al. PNAS 83, 299–302 [1986] and Broze,G. H. et al., J.Biol.Chem. 260 [20], 10917–10920 [1985]); bovine brain (Bach, R. et al., J. Biol. Chem. 256, 8324–8331 [1981]); human placenta (Bom, V. J. J. et al., Thrombosis Res. 42:635–643 [1986]; and, Andoh, K. et al., Thrombosis Res. 43:275–286 [1986]); ovine brain (Carlsen, E. et al., Thromb. Haemostas. 48[3], 315–319 [1982]); and, lung (Glas, P. and Astrup, T., Am. J. Physiol. 219, 1140–1146 [1970]. It has been shown that bovine and human tissue thromboplastin are identical in size and function. See for example Broze, G. H. et al., J. Biol. Chem. 260(20), 10917–10920 (1985). It is widely accepted that while there are differences in structure of tissue factor protein between species there are no functional differences as measured by in vitro coagulation assays. Guha et al. supra. Furthermore, tissue factor isolated from various tissues of an animal, e.g. dog brain, lung, arteries and vein was similar in certain respects such as, extinction coefficient, content of nitrogen and phosphorous and optimum phospholipid to lipid ratio but differed slightly in molecular size, amino acid content, reactivity with antibody and plasma half life. Gonmori, H. and Takeda, Y., J. Physiol. 229(3), 618–626 (1975). All of the tissue factors from the various dog organs showed clotting activity in the presence of lipid. Id. It is widely accepted that in order to demonstrate biological activity, tissue factor must be associated with phospholipids. Pitlick, F. A., and Nemerson, Y., Biochemistry 9, 5105–5111 (1970) and Bach,R. et al. supra. at 8324. It has been shown that the removal of the phospholipid component of tissue factor, for example by use of a phospholipase, results in a loss of its biological activity. Nemerson, Y., J.C.I. 47, 72–80 (1968). Relipidation can restore in vitro tissue factor activity. Pitlick, F. A. and Nemerson, Y., Biochemistry 9, 5105–5113 (1970) and Freyssinet, J. M. et al., Thrombosis and Haemostasis 55, 112–118 [1986].

Infusion of tissue factor has long been believed to compromise normal haemostasis. In 1834 the French physiologist de Blainville first established that tissue factor contributed directly to blood coagulation. de Blainville, H. Gazette Medicale Paris, Series 2, 524 (1834). de Blainville also observed that intravenous infusion of a brain tissue suspension caused immediate death which he observed was correlated with a hypercoagulative state giving rise to extensively disseminated blood clots found on autopsy. It is now well accepted that intravenous infusion of tissue thromboplastin induces intravascular coagulation and may cause death in various animals. (Dogs: Lewis, J. and Szeto I. F., J. Lab. Clin. Med. 60, 261–273 (1962); rabbits: Fedder, G. et al., Thromb. Diath. Haemorrh. 27, 365–376 (1972); rats: Giercksky, K. E. et al., Scand. J. Haematol. 17, 305–311 (1976); and, sheep: Carlsen,E. et al., Thromb. Haemostas. 48, 315–319 [1982]).

In addition to intravascular coagulation or a hypercoagulative state resulting from the exogenous administration of tissue factor, it has been suggested that the intravascular release or exposure of tissue thromboplastin may initiate disseminated intravascular coagulation (DIC). Prentice, C. R., Clin. Haematol. 14(2), 413–442 (1985). DIC or localized intravascular coagulation may arise in various conditions such as shock, septicaemia, cardiac arrest, post-operative deep vein thrombosis, pulmonary embolism, unstable angina, post-angioplasty thrombosis, extensive trauma, bites of poisonous snakes, acute liver disease, major surgery, burns, septic abortion, heat stroke, disseminated malignancy, pancreatic and ovarian carcinoma, promyelocytic leukemia, myocardial infarction, neoplasms, systemic lupus erythematosus, renal disease and eclampsia. Present treatment of DIC includes transfusion of blood and fresh frozen plasma; infusion of heparin; and removal of formed thrombi. The foregoing clinical syndromes suggest that endogenous release or exposure of tissue factor can result in severe clinical complications. Andoh, K. et al., Thromb. Res. 43, 275–286 (1986). Efforts were made to overcome the thrombotic effect of tissue thromboplastin using the enzyme thromboplastinase. Gollub, S. et al., Thromb. Diath. Haemorh. 7, 470–479 (1962). Thromboplastinase is a phospholipase and would presumably cleave the phospholipid portion of tissue factor. Id.

An object of the present invention is to provide an effective therapy for myocardial infarction which limits necrosis by permitting early reperfusion and by preventing reocclusion.

A further object of this invention is to provide a therapeutic composition for treatment of myocardial infarction and prevention of reformation of fibrin-platelet clots, i.e. reocclusion.

Yet another object of this invention is to provide an anticoagulant therapeutic, that is an antagonist to tissue factor protein, to neutralize the thrombotic effects of endogenous release of tissue thromboplastin which may result in a hypercoagulative state. Particularly, such an anticoagulant, that is an antagonist to tissue factor protein, would neutralize the hypercoagulant to tissue factor protein, would neutralize the hypercoagulant effects of endogenously released or exposed tissue thromboplastin by inactivating tissue factor protein. Such a tissue factor protein antagonist can be an antibody or other protein or small organic molecule that specifically inhibits tissue factor activity.

SUMMARY OF THE INVENTION

This invention is based in part on the novel and unexpected observation that tissue factor was found to be present in atherosclerotic plaques. It was observed that tissue factor was present in the plaque in greater amounts than in normal vessels. It was also observed that tissue factor mRNA was present in both mesenchymal like intimal cells as well as in macrophages and cells adjacent to the cholesterol clefts within the atherosclerotic plaque.

Accordingly, in one aspect the invention is directed to administration of a pharmaceutical composition comprising a tissue factor protein antagonist and a thrombolytic agent. In another aspect the invention provides a method of treatment for myocardial infarction which comprises administering to a patient in need of such treatment:

a) a tissue factor protein antagonist capable of preventing potential clot reformation, in a therapeutically effective amount to prevent such reformation; either alone or in combination with b) a thrombolytic agent, in a therapeutically effective amount to dissolve a fibrin-platelet clot; or with c) an anticoagulant or anti-platelet agent, such as aspirin, or an antagonist to platelet glycoprotein $II_b/III_a$ aggregrating factor, in a therapeutically effective amount to prevent clotting or platelet aggregation, respectively.

A further aspect of this invention is directed to an anticoagulant to neutralize the coagulant effects of endogenously released or exposed tissue thromboplastin by inactivating tissue factor protein. Yet another aspect of this invention is directed to an anti-atherosclerotic agent to neutralize the effects of endogenously released or exposed tissue thromboplastin in the formation of atherosclerotic plaques by inactivating tissue factor protein.

BRIEF DESCRIPTION OF THE DRAWINGS

FIG. 4. Procoagulant activity of a carotid endarterectomy specimen measured using a modified one-stage prothrombin time assay in Factor XII deficient plasma. The procoagulant activity of the tissue was significantly reduced by preincubation with a neutralizing polyclonal antibody RD010.

DETAILED DESCRIPTION

Figure 1A:
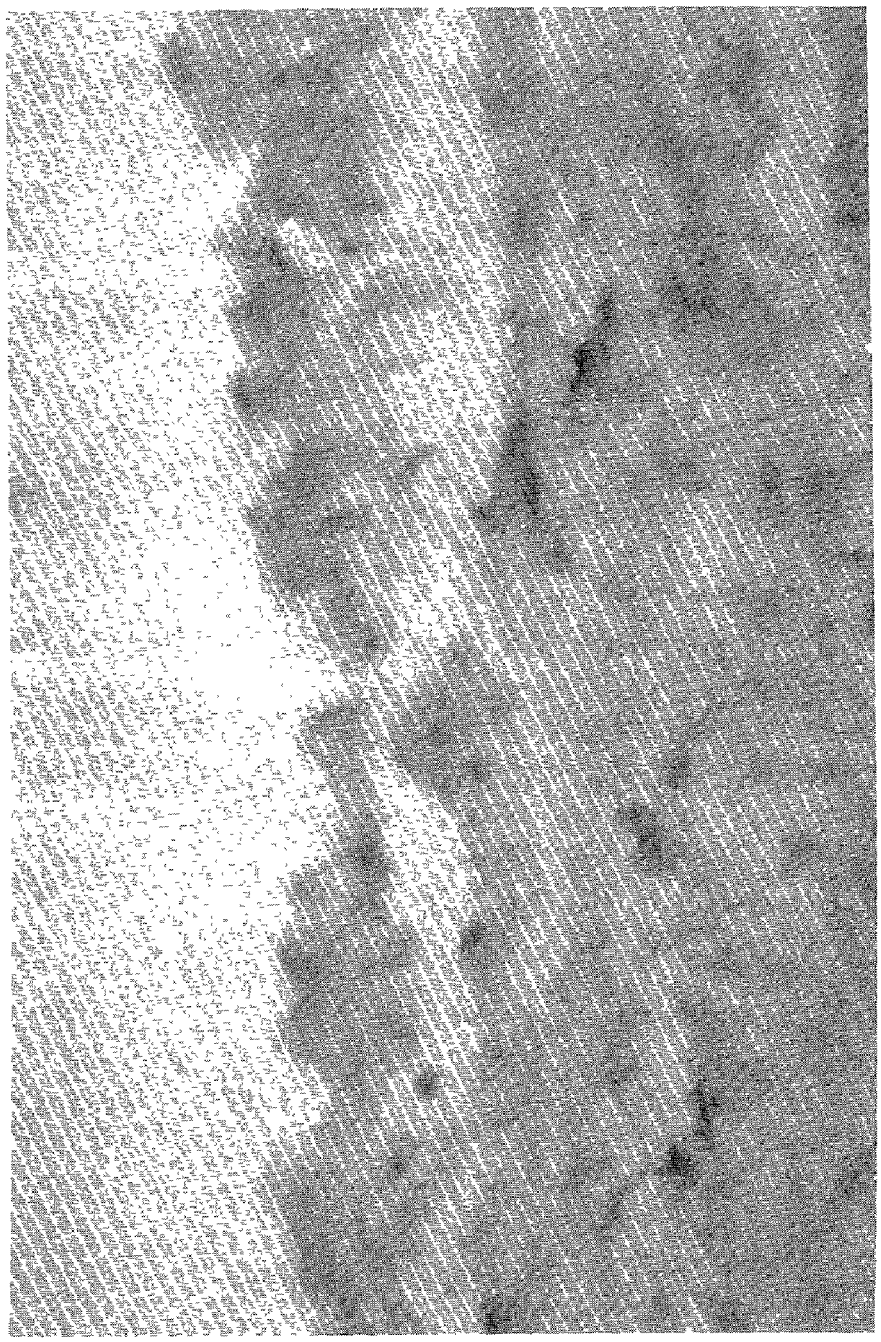
FIGS. 1a–c (herein referred to as FIG. 1). Localization of tissue factor in the normal human saphenous vein. Cells containing tissue factor protein were detected by immunocytochemistry using the Vectastain alkaline phosphatase method (positive cells stain red). Scattered cells in the tunica media were lightly stained by the RD010 antibody whereas endothelial cells lining the normal vessel were always negative (panel A magnification 500×). Strong immunohistochemical staining was always seen in the adherent adventitial fibroblasts (panel B, magnification 500×). In situ hybridization using a specific $^{35}$S-labelled tissue factor mRNA probe confirmed that there were scattered tissue factor producing cells in the media (panel C, magnification 310×) and adventitia (not shown).

As used herein, the term "tissue factor protein antagonist" refers to a substance which inhibits or neutralizes the procoagulant activity of tissue factor. Such antagonists accomplish this effect in various ways. First, one class of tissue factor protein antagonists will bind to tissue factor protein with sufficient affinity and specificity to neutralize tissue factor protein such that it cannot bind to factor VII or VII$_a$ nor effect the proteolysis of factors IX or X when in complex with factor VII or VII$_a$. Included within this group of molecules are antibodies and antibody fragments (such as, for example, F(ab) or F(ab')$_2$ molecules). Another class of tissue factor antagonists will neutralize tissue factor activity by creating a complex of molecules, e.g., the naturally occurring tissue factor inhibitor "LACI" which comprises lipoprotein associated coagulation inhibitor which forms an inactive complex of tissue factor, factor VII, factor X and phospholipid (Broze, G. J. et al., PNAS 84:1886–1890 [1987]). Another class of tissue factor protein antagonists are fragments of tissue factor protein, fragments of factor VII or small organic molecules, i.e. peptidomimetics, that will bind to tissue factor, thereby inhibiting the formation of the tissue factor-factor VII complex or inhibit the activation of factors IX and X by tissue factor. Yet another class of tissue factor protein antagonists will inactivate tissue factor protein or the tissue factor/factor VII$_a$ complex by cleavage, e.g. a specific protease. A fifth class of tissue factor protein antagonists block the binding of tissue factor protein to factor VII, e.g., a factor VII antibody directed against a domain of factor VII which is involved in the activation of factor VII by tissue factor.

Tissue factor protein antagonists are useful in the treatment of myocardial infarction to prevent reocclusion or in the therapy of various coagulation disorders as described above, e.g., DIC occurring during severe infections and septicemias, various malignancies, e.g., small cell lung carcinoma, eclampsia, deep vein thrombosis, after surgery or trauma, instead of or in combination with other anticoagulants such as heparin.

An example of an antagonist which will neutralize tissue factor protein is an antibody to tissue factor protein. Tissue factor protein neutralizing antibodies are readily raised in animals such as rabbits or mice by immunization with tissue factor protein in Freund's adjuvant followed by boosters as required. Immunized mice are particularly useful for providing sources of B cells for the manufacture of hybridomas, which in turn are cultured to produce large quantities of inexpensive anti-tissue factor protein monoclonal antibodies. Such tissue factor protein monoclonal antibodies have been prepared by Carson, S. D. et al., Blood 66(1), 152–156 (1985).

As used herein, "tissue factor protein" refers to a protein capable of correcting various bleeding disorders particularly those associated with deficiencies in coagulation factors. Tissue factor protein is distinct from tissue factor or tissue thromboplastin in that it lacks the naturally occurring lipid portion of the molecule. Tissue factor protein also includes tissue factor protein associated with phospholipid which lipid is distinct from the naturally occurring lipid associated with tissue thromboplastin and which displays coagulation-inducing capability without the concomitant toxicity observed with the lipidated protein.

Tissue factor is released or exposed by cell damage and activates factors IX and X in the presence of factor VII or VII$_a$ and calcium. The activation of factor X by the extrinsic pathway of coagulation has an absolute requirement for tissue factor. Silverberg, S. A., et al., J. Biol. Chem. 252, 8481–8488 (1977). Until the discovery of this invention, the cellular distribution of tissue factor protein producing cells within tissues from which tissue factor had been isolated was unknown. Nor was it known that tissue factor protein is present in atherosclerotic plaques in amounts exceeding that in normal tissues. Nor was it known that rupture of an atherosclerotic plaque may precipitate clot formation by exposure of tissue factor.

The term "thrombolytic agent" is meant to refer to any agent capable of either dissolving a fibrin-platelet clot, or inhibiting the formation of such a clot. Examples of thrombolytic agents include streptokinase, prourokinase, urokinase, and tissue-type plasminogen activator ("t-PA"). Although natural t-PA (Collen, et al., EP application publication no. 041,766, filed Jun. 10, 1981) may be employed, it is preferable to employ recombinant t-PA (Goeddel et al., EP application publication no. 093,619, filed May 4, 1983). The invention may additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

The term "anticoagulant" is meant to refer to any agent capable of prolonging the prothrombin and partial thromboplastin time tests and reducing the levels of prothrombin and factors VII, IX and X. Anticoagulants typically include cormarin derivatives and heparin as well as aspirin, which may also be referred to as an antiplatelet agent.

The tissue factor protein antagonist of the present invention is provided with a goal of preventing potential reformation of fibrin-platelet clots. Such fibrin-platelet clots may form as a consequence of the cessation of treatment with a thrombolytic agent. Advanced human atherosclerosis is characterized by intimal smooth muscle cell proliferation accompanied by accumulation of fats and inflammatory cells including macrophages and T cells within the atherosclerotic plaque (Ross,R., N.Engl. J. Med. 314:488–500 [1986]; Gown et al., Am. J. Pathol. 125:191–207 [1986]; Jonasson et al., Arteriosclerosis 6:131–138 [1986]). Thrombosis is commonly the critical event which converts an asymptomatic atherosclerotic plaque into a symptomatic one (Falk,E. Br. Heart J. 50:127–134 [1983]; Sherman et al., N. Engl. J. Med. 315:913–919 [1986]; Impesato, A. M. et al., Ann. Surg. 197:195–203 [1983]) whereas non-diseased arteries hardly ever become thrombosed. It has been suggested that plaque rupture is the integral event that precipitates clot formation (Forrester et al., Circulation 75:505–513 [1987]). An occlusive mural thrombus accompanies most cases of acute myocardial infarctions (Buja, L. M. et al., Am. J. Cardiol. 47:343–356 [1981]; Horie, T. et al., Brit. Heart. J. 40:153–161 [1978]). Plaque rupture or cracking is normally found to underlie such thrombi, and in many cases the thrombus is seen to extend into the region of the necrotic core of the plaque extruding through such cracks. This is true of both the coronary (Falk, Br. Heart J. 50:127–134 [1983]; Chapman, I., Arch. Path. 30:256–261 [1965]; Drury, J. Path. Bact. 67:207–215 [1954]) and cerebral arteries (Constantinides, J. Arch. Pathol. 83:422–428 [1967]). Until this invention, the source of the thrombogenicity of the plaque has not previously been determined but was previously assumed to occur when blood components come into contact with fats or the collagen matrix within the plaque. The current studies establish that there is a) significant synthesis of tissue factor protein in atherosclerotic plaques; b) that tissue factor protein accumulates in the necrotic core and is found in foam cell rich regions of the plaque; and c) that there is in the plaque procoagulant activity due to tissue factor as determined by in vitro coagulation assays that is significantly reduced by tissue factor protein antibodies. These results indicate that overproduction and/or trapping of tissue factor protein in the atherosclerotic plaque may play a significant role in thrombosis associated with human atherosclerotic vessels and clot reformation following thrombolytic therapy in the treatment of myocardial infarction.

The tissue factor protein antagonist and the thrombolytic agent of the present invention are intended to be provided to the recipient in combination. Medicaments are considered to be provided "in combination" with one another if they are provided to the patient concurrently, or if the time between the administration of each medicament is such as to permit an overlap of biologic activity. It is preferable to provide the tissue factor protein antagonist to the patient prior to the administration of the thrombolytic agent.

An amount of tissue factor protein antagonist capable of preventing partial reformation of a clot when provided to a patient is a "therapeutically effective" amount. In order to prevent potential clot reformation tissue factor protein antagonist will be provided using an amount per kilogram of patient weight determined by the ordinarily skilled physician. This dosage may be administered, in one embodiment, over a period of between 75–180 minutes, by continual intravenous infusion. The tissue factor protein antagonist may be given by cardiac catheterization or by an intravenously injectable bolus at a dose of about in the range of 0.01–25.0 milligrams per kilogram of patient weight. If the tissue factor protein antagonist is provided by an intravenously injected bolus, a single bolus may be sufficient to prevent potential clot reformation.

The thrombolytic agent is provided in order to cause the lysis of an occluding thrombus. An amount of thrombolytic agent capable of causing such lysis is a "therapeutically effective" amount. The thrombolytic agent of the present invention is preferably provided at a dose of between 0.01–2.5 mg per kg of patient weight. In one embodiment, the thrombolytic agent is provided over a prolonged period (i.e., from about 60 to about 120 minutes). In a preferred embodiment, the thrombolytic agent of the present invention is provided as an intravenously injected bolus containing between 0.01–1.0 mg/kg, and most preferably between 0.1–1.0 mg/kg. The thrombolytic agent of the present invention may be dissolved in any physiologically tolerated liquid in order to prepare an injectable bolus. It is, however, preferable to prepare such a bolus by dissolving the thrombolytic agent in an appropriate buffer.

A patient treated according to the preferred embodiment will, therefore, receive an intravenously injected bolus of the tissue factor protein antagonist in combination with an intravenously injected bolus of the thrombolytic agent. Importantly, the use of the preferred treatment results in the dissolution of the occluding thrombus at a rate which greatly exceeds the rate of thrombus dissolution when either the tissue factor protein antagonist or the thrombolytic agent is provided by infusion. Additionally, the risk of reocclusion is substantially reduced. A patient treated according to the preferred embodiment may not require heparin which is generally required with a maintenance infusion t-PA treatment.

These unexpected findings provide a method of treatment in which the administration of a bolus of a tissue factor protein antagonist in combination with the administration of a bolus of a thrombolytic agent are capable of dissolving an occluding thrombus and minimizing the risk of reocclusion.

As would be apparent to one of ordinary skill in the art, the required dosage of the tissue factor protein antagonist or thrombolytic agent will depend upon the severity of the condition of the patient, and upon such criteria as the patient's height, weight, sex, age, and medical history.

The tissue factor protein antagonist or thrombolytic agent of the present invention can be formulated according to known methods to prepare pharmaceutically useful compositions, such as by admixture with a pharmaceutically acceptable carrier vehicle. Suitable vehicles and their formulation are described, for example, in Remington's Pharmaceutical Sciences (16th ed., Osol, A. (ed.), Mack, Easton, Pa. [1980]). In order to form a pharmaceutically acceptable composition suitable for effective administration, such compositions will contain an effective amount of the tissue factor protein antagonist or thrombolytic agent, either alone, or with a suitable amount of carrier vehicle. Although the tissue factor protein antagonist of the present invention may be dissolved in any physiologically tolerated liquid in order to prepare an injectable bolus, it is preferable to prepare such a bolus by dissolving the tissue factor protein antagonist in saline.

Additional pharmaceutical methods may be employed to control the duration of action. Control release preparations may be achieved by the use of polymers to complex or adsorb the tissue factor protein antagonist or thrombolytic agents of the present invention. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agent in microcapsules prepared, for example, by coacervation techniques or by interfacial polymerization, for example, by the use of hydroxymethylcellulose or gelatin-microcapsules or poly (methylmethacrylate) microcapsules, respectively, or in a colloid drug delivery system, for example, liposomes, albumin microspheres, microemulsions, nanoparticles, nanocapsules, or in macroemulsions. Such teachings are disclosed in Remington's Pharmaceutical Sciences (1980).

The thrombolytic agent or tissue factor protein antagonist may be provided to a patient by means well known in the art. Such means of introduction include oral means, intranasal means, subcutaneous means, intramuscular means, intravenous means, intra-arterial, including catheterization, means or parenteral means. In the most preferred method of treatment for myocardial infarction, a patient is provided with a bolus (intravenously injected) at a dosage determined by the ordinarily skilled physician taking into account various criteria which establish that particular patient's clinical condition.

It is also contemplated that the tissue factor protein antagonist could be labeled with a detectable indicator and injected into a host's bloodstream and subsequently assayed for its presence in an atherosclerotic plaque. The tissue factor protein antagonist may be labeled with any known indicator detectable in a host's bloodstream, e.g., $^{131}I$, $^{125}I$, selenium, technetium or bifunctional chelates. The tissue factor protein antagonist can also be labeled with a nonradioactive indicator detectable by, e.g., nuclear magnetic resonance, or other means in the art. The labeling of the tissue factor protein antagonist can be achieved using methods known to the ordinarily skilled artisan, e.g., in the case of $^{125}I$ using lactoperoxidase or iodogen techniques. using methods known to the ordinarily skilled artisan, e.g., in the case of $^{125}I$ using lactoperoxidase or iodogen techniques.

Having now generally described this invention, it will be better understood by reference to certain specific examples which are included herein for purposes of illustration only, and are not intended to limit the invention, unless specified.

EXAMPLE 1

General Materials and Methods

TRITON™ X-100 was from Calbiochem. San Diego, Calif. All chemicals and reagents for preparative and analytical sodium dodecyl sulfate polyacrylamide gel electrophoresis (SDS-PAGE) were obtained from Bio-Rad Laboratories, Richmond, Calif. Factor IXa/Factor X reagent and S2222/I2581 were obtained from Helena Laboratories (Kabi Coatest kit, Helena Laboratories, Beaumont, Calif., Catalogue No. 5293). YM 10 ultrafiltration membranes were from Amicon. Factor VII was purchased from Sigma Chemical Crude phosphotidylcholine (lecithin granules from soya bean) were obtained from Sigma, St. Louis, Mo. All other chemicals were of reagent grade or better.

Purification of Tissue Factor Protein

Tissue factor protein was purified using immunoaffinity purification using an IgG monoclonal antibody that binds human tissue factor protein.

Human tissue factor protein was synthesized in recombinant culture as described in European Patent Application No. 88301190.0, filed Feb. 12, 1988. The following immunogens were injected into a BALB/c mouse (29.1.B) according to the schedule described below: recombinant human tissue factor protein (rTF) (0.72 mg/ml having a specific activity 4687 U/mg) OR (0.07 mg/ml having a specific activity 17040 U/mg); recombinant tissue factor protein obtained from a tissue factor-gD fusion cleaved by thrombin to remove the herpes-gD sequences from the amino terminal end (rTF:gDThr) (4300 U/ml) and recombinant tissue factor-herpes-gD fusion (rTF-gD) (approximately 740 U/ml) on the following immunization schedule:

| Day | Administration Route | Immunogen |
| --- | --- | --- |
| 1. | subcutaneous (sc) | 0.25 ml of r-TF in Freund's complete adjuvant |
| 14. | half sc and half intraperitoneal (ip) | 0.25 ml r-TF in incomplete Freund's adjuvant |
| 28. | I.P. | 0.25 ml of r-TF in PBS |
| 42. | I.P. | 0.25 ml of r-TF in PBS |
| 62. | I.P. | 0.25 ml of r-TF in PBS |
| 75. | I.P. | 0.52 ml of r-TF-gD in PBS |
| 85. | I.p. | 0.5 ml of r-TF-gDThr in PBS |

The anti-TF titer assayed by radio-immunoprecipitation (RIP) and ELISA increased gradually throughout the immunizations to day 85.

The RIP assay used 0.005 ml of sera from immunized and nonimmunized mice dilated with 0.495 ml of PBSAT (PBS containing 0.5% bovine serum albumin [BSA] and 0.1% TRITON™ X-100). 50,000 cpm of $^{125}I$-rTF was added and the mixture was incubated for 2 hr at room temperature. $^{125}I$-rTF complexed with antibody was precipitated by incubating for 1 hr at room temperature with 0.05 ml of SPA beads. The SPA beads consisted of staphylococcal protein A bound to SEPHAROSE™ CL-4B beads that had been pre-incubated with rabbit antimouse IgG and stored in PBS, 0.1% BSA and 0.02% $NaN_3$. The beads were pelleted, washed three times with PBSAT and counted in a gamma counter.

The ELISA consisted of 0.1 ml of rTF (0.5 mu.g/ml) in carbonate buffer pH 9.6 adsorbed to microtiter wells for 2 hr at 37° C. Further non-specific adsorption to the wells was blocked for 1 hr at 37° C. with PBSA (PBS containing 5% BSA). The wells were washed 3 times with PBST (PBS containing 0.1% TWEEN™ 20) and the serum samples diluted in PBSAT was added and incubated 2 hrs. at 22. degree. C. The wells were washed 3 times with PBSAT. 0.1 ml of goat anti-mouse immunoglobulin conjugated to horseradish peroxidase was added to each well and incubated for 1 hr at room temperature. The wells were washed again and o-phenylenediamine dihydrochloride was added as substrate and incubated for 25 minutes at room temperature. The reaction was stopped with 2.5 M $H_2SO_4$ and the absorbance of each well was read at 492 nm.

On day 89 the spleen from mouse 29.1.B was harvested, disrupted and the spleen cells fused with X63-Ag8.653 (ATCC CRL 1580) non-secreting mouse myeloma cells using the PEG fusion procedure of S. Fazakas de St. Groth et al., J. Immun. Meth., 35:1–21 (1980). The fused culture was seeded into 4 plates each containing 96 microtiter wells and cultured in HAT (hypoxanthine, aminopterin and thymidine) media by conventional techniques (Mishell and Shiigi, *Selected Methods in Cellular Immunology*, W. H. Freeman & Co., San Francisco, pp. 357–363 [1980]). The anti-TF activity of culture supernatants was determined by ELISA and RIA. Twelve stable fusions (hybridomas) secreted anti-TF as determined by ELISA or antigen capture RIA described below. The hybridomas were expanded and cloned by limiting dilution using published procedures (Oi, V. J. T. & Herzenberg, L. A., "Immunoglobulin Producing Hybrid Cell Lines" in *Selected Methods in Cellular Immunology*, p. 351–372, Mishell, B. B. and Shiigi, S. M. [eds.], W. H. Freeman & Co. [1980]). Selection of clones was based on: macroscopic observation of single clones, ELISA and RIA. The antibody was isotyped using a Zymed isotyping kit according to the accompanying protocol (Zymed Corp.) Large quantities of specific monoclonal antibodies were produced by injection of cloned hybridoma cells in pristane primed mice to produce ascitic tumors. Ascites were then collected and purified over a protein-A SEPHAROSE™ column.

Antigen capture RIA methodology used $^{125}I$ labeled tissue factor protein with the lactoperoxidase-enzymobeads (BIO-RAD, Richmond, Calif.) following the vendor's suggested protocol. Polystyrene "strip wells" were coated with 100 $\mu$l/well of goat anti-mouse IgG (H & L chain specific, Boehringer Mannheim) at 5 $\mu$g/ml in pH 9.6 carbonate buffer for 1 hour at 37° C. The strips were washed with PBSAT and incubated with 50,000 CPM $^{125}I$-TF in 100 $\mu$l BPBST for 2 hours at 22° C. The strips were washed and individual wells were counted on a 20/20 gamma counter to determine percentage of input counts bound.

The foregoing method for immunization and screening for anti-tissue factor antibody is exemplary. For example, immunization could be carried out using a particular antigen such as r-tissue factor protein, gD-tissue factor fusion or thrombin cleaved gD-tissue factor fusion. The immunization protocol could be modified by altering the route of administration, the method of in vitro immunization, various conjugation or adjuvant techniques or by selecting from various available sources species of B cells. Antibody could be screened for neutralization of tissue factor activity using, for example, the chromogenic assay described below. Screening for neutralizing antibodies could be carried out by testing the harvested supernatant in the chromogenic assay rather than using an ELISA or RIA.

Approximately 5 ml of ascites fluid was centrifuged at 3000 rpm in a Sorvall 6000 at 4° C. for 10 min. The clear layer of pristane and the layer of lipid was removed with a pasteur pipet. The ascites fluid was transferred to a 50 ml centrifuge tube. The ascites fluid was sterile filtered through a 0.45$\mu$ filter. 1.11 gram of KCl was added to the ascites to yield a final concentration of 3M KCl.

The ascites was loaded onto a 10 ml column containing SPA SEPHAROSE™ (Fermentech). The column was washed with 3M KCl. The mouse IgG was eluted with 3 to 4 column volumes of 0.1M acetic acid in 0.15M NaCl pH 2.8.

The antibody D3 was coupled to CNBr SEPHAROSE™ according to the manufacturer's instructions at 3 mg IgG per ml of SEPHAROSE™. (See Pharmacia Co. instruction manual). Transfected 293S cells were grown in a 1:1 mixture of Ham's F-12 (w/o glycine, hypoxanthine and thymidine) and DMEM (w/o glycine). Additions to the basal medium include: 10% dialyzed or diafiltered fetal calf serum, 50 nM methotrexate, 2.0 mM L-glutamine and 10 mM HEPES buffer.

A frozen vial of 293S (63/2S CISTF) is thawed in a tissue culture flask containing the described medium. When the culture reaches confluency it is trypsinized with trypsin-EDTA mixture and a small portion of the cell population was used to inoculate larger flasks. Cultures were monitored daily by phase microscopy to determine growth (percent confluency), morphology and general health. When roller-bottle cultures were confluent (usually within 5–7 days), the cells were trypsinized and counted. Cells were enumerated and their viabilities determined by the trypan blue exclusion technique. Typical cell numbers from a confluent 850 $cm^2$ rollerbottle were between 1 to $4 \times 10^8$ cells. Cells were suspended in 0.01M sodium phosphate, 0.15M NaCl. Cells were collected by centrifugation at 5000 rpm. Cells were resuspended in 50 mls TBS containing 1% TRITON™ X per flask. Cultures were incubated one hour at room temperature and then centrifuged 8000$\times$ g for 20 min. Supernatant was loaded onto the D3 SEPHAROSE™ column described above. The column was washed and eluted with 0.1M acetic acid, 150 mM NaCl and 0.05% TWEEN™ 80.

Assay for Tissue Factor Protein

1. Chromogenic Tissue Factor Assay.

All tissue factor protein samples were relipidated prior to assay. As discussed above tissue factor has an absolute requirement for phospholipid to exhibit activity in in vitro assay systems (Pitlick and Nemerson, Supra). Lecithin granules were homogenized in Tris 0.05 M, 0.1 M NaCl pH7.4 (TBS) containing 0.25% sodium deoxycholate to a concentration of 1 mg/ml. This solution (PC/DOC) was used to relipidate tissue factor as follows. Tissue factor protein was diluted into TBS containing 0.1% bovine serum albumin (TBSA). Fifty microliters were placed in a 12$\times$75 mm polystyrene test tube and 50 $\mu$l PC/DOC solution was added. Three hundred and fifty (350) microliters TBSA were then added along with 25 $\mu$l 100 mM $CdCl_2$. This relipidation mixture was allowed to incubate at 37° C. for 30 min.

For the chromogenic assay, relipidated tissue factor protein samples were diluted in TBSA. Ten microliters were placed in a test tube with 50 $\mu$l of the factor $IX_a$/factor X reagent and 2 $\mu$l of a solution of purified factor VII, 30 units/ml. The tubes were warmed to 37° C. and 100 $\mu$l 25 mM $CaCl_2$ were added. Samples were incubated for 5 min. at 37° C. prior to the addition of 50 $\mu$l chromogenic substrate S2222 containing the synthetic thrombin inhibitor I2581. The reaction was allowed to proceed for 10 min. and was stopped by the addition of 100 $\mu$l 50% glacial acetic acid solution. Absorbance was detected at 405 nm. A standard curve was constructed using rabbit brain thromboplastin (commercially available from Sigma, St. Louis, Mo. catalogue #T0263) arbitrarily assigning this reagent as having 100 tissue factor units/ml. Dilutions were made from 1:10 to 1:1000. Absorbance was plotted on the abscissa on semilog graph paper with dilution of standard plotted on the ordinate.

2. One Stage Assay for Tissue Factor Activity.

100 μl haemophilic plasma were added to 10 μl of relipidated or lipid free tissue factor or TBSA as control in a siliconized glass tube to prevent non-specific activation through the contact phase of coagulation. The reactants were warmed to 37° C. and 100 μl 25 mM CaCl$_2$ were added and clot formation timed. Hvatum, Y. and Prydz, H., Thromb. Diath. Haemorrh. 21, 217–222 (1969).

Tissue Preparation

Normal human saphenous veins and internal mammary arteries were obtained during coronary artery bypass surgery. Human atherosclerotic plaques were obtained from patients undergoing carotid endarterectomy surgery. Endarterectomy surgery consists of removal of an atherosclerotic plaque and some of the underlying smooth muscle. Additional normal tissue from a sacrificed Rhesus monkey, including samples of normal organs and vessels, were prepared as described for screening of tissue factor expression.

The tissue samples were removed at surgery and immersed in freshly prepared 4% paraformaldehyde in 0.1M sodium phosphate (pH 7.4). The tissue was fixed at 4° C. for 3 hrs. to overnight and then immersed in 15% sucrose phosphate buffered saline (PBS) for 2–4 hrs. at 4°C. to act as a cryoprotectant. The tissue was then embedded in an embedding medium for frozen tissue specimens ("OCT", Miles Laboratories) blocks and stored at −70° C. There was no loss of immunoreactivity or mRNA available for hybridization during this time. The tissue was sectioned at 10 μm thickness using a cryostat, thaw-mounted onto poly-lysine coated microscope slides and immediately refrozen and stored at −70° C. with dessicant. Additional atherosclerotic plaque tissue was snap frozen at surgery for use in coagulation assays to assess tissue factor activity.

In Situ Hybridization

In situ hybridizations were carried out as described previously (Rosenthal et al., EMBO J. 6:3641–3646 [1987]; Wilcox et al., Methods Enzymol. 124:510–533 [1986]). Prior to hybridization the sections were pretreated with paraformaldehyde (10 min.), proteinase K (1 μg/ml) (10 min.), and prehybridized for 1 to 2 hrs. in 50 μl of pre-hybridization buffer (0.3 M NaCl, 20 mM Tris pH 8.0, 5 mM EDTA, 1× Denhardt's solution, 10% dextran sulfate and 10 mM dithiothreitol). The hybridizations were started by adding 600,000 CPMs of a tissue factor $^{35}$S riboprobe in a small amount of pre-hybridization buffer. After hybridization the sections were washed with 2×SSC (2×10 min.) (1×SSC=150 mM NaCl, 15 mM Na citrate, pH 7.0), treated with RNase (20 μg/ml, 30 min. room temperature), washed in 2×SSC (2×10 min.), followed by a high stringency wash in 0.1×SSC at 52° C. for 2 hrs. All SSC solutions up to this point of the procedure contained 10 mM β-mercaptoethanol and 1 mM EDTA to help prevent non-specific binding of the probe. The tissue was then washed in 0.5×SSC without β-mercaptoethanol (2×10 min.) and dehydrated by immersion in graded alcohols containing 0.3M ammonium acetate. The sections were dried and coated with NTB2 nuclear emulsion (Kodak, Rochester, N.Y.) and exposed in the dark at 4° C. for 4 to 8 weeks. After developing, the sections were counterstained with hematoxylin and eosin. The sections were developed at 15° C. by treating the slides for 3 minutes in D19 developer diluted 1:1 with water, (Kodak), 20 seconds in water and 3 minutes in fixer. Slides were rinsed and counter-stained.

A probe specific to human tissue factor (Fisher et al., Thrombosis Res. 48:89–99 [1987]) was labelled by transcription (Melton et al., Nucl. Acids Res. 12:7035–7056 [1984]) using [$^{35}$S]-labelled UTP (specific activity 1200 Ci/mmol, Amersham). This was a 1.2 Kb probe and included the entire coding sequence for human tissue factor extending from nucleotide 1 in the 5' flanking region to an NcoI site at nucleotide 1224 in the 3' untranslated region (Fisher et al., supra). The final specific activity of this probe was 300 Ci/mmol.

Immunocytochemistry

Immunocytochemistry was performed according to the manufacturer's direction using the VECTASTAIN® ABC alkaline phosphatase system (Vector, Inc., Burlingame, Calif.). The final reaction product was stained with the alkaline phosphatase substrate kit I to give a final stain that appeared red. The anti-tissue factor protein antibody used was antibody RD010, described in Example 2 below.

An IgG fraction of the preimmune serum was used as a control for the tissue factor protein immunohistochemistry at the same IgG concentration as RD010. This was prepared by passing the preimmune serum over a protein A SEPHAROSE™ column. Frozen aliquots of all the antibody preparations were stored at −20° C. until use.

Antibodies specific for human macrophages (HAM56, Gown, A. M. et al. Am. J. Pathol. 125:191–207 [1986]) or human endothelial cells (anti-Ulex Lectin, commercially available from Vector, Inc.) were also used to aid in cell identification.

Coagulation Assays

Procoagulant activity of human plaque tissue obtained during carotid endarterectomy surgery was measured using a two-stage clotting assay (Pitlick, F. A. and Nemerson, Y., Methods Enzymol., 45: 37–48 [1976]). A small piece of snap-frozen, unfixed plaque was thawed and incubated with 20 ul factor VII (Sigma, minimum activity 10 U ml$^{-1}$), 3 ul factor X (Sigma, minimum activity 10 U ml$^{-1}$) and 25 ul 50 mM calcium chloride, for 60 sec at 37° C. A 20 ul aliquot was then removed and added simultaneously with 80 ul, 25 mM CaCl$_2$ to 100 ul of factor XII deficient plasma plus 100 ul rabbit cephalin at 37° C. Time to fibrin formation was noted visually. When reused, plaque was removed from the incubation mixture rinsed with Tris buffer (50 mM, pH 7.5) and the incubation repeated. Neutralizing effects of an affinity purified polyclonal antibody, RD010 were measured by preincubation of plaque segments in Tris buffer (50 mM, pH 7.5) containing antibody for 10 min. at 37° C. before addition of factor VII, X and calcium chloride. All values are expressed as mean ±S.E.M.

EXAMPLE 2

Production of Tissue Factor Protein Antagonists

The tissue factor protein antagonist, antibody RD010, was an affinity purified polyclonal antibody raised in rabbits. The RD010 was prepared by immunization of rabbits with tissue factor protein in Freund's adjuvant followed by boosters as required. Rabbits were immunized with recombinant human tissue factor protein produced in 293S cells as a fusion protein (see European Patent Application No. 88301190.0, filed Feb. 12, 1988). The immune serum was purified by affinity chromatography on a recombinant human tissue factor-sepharose column. This antibody was shown to be monospecific on a western blot, to neutralize tissue factor activity, and immunoprecipitate tissue factor protein. This antibody was used at a dilution of 4.4 µg/ml for immunocytochemistry while 1.0–100 µg/ml was used for in vitro tissue factor inhibition studies.

Human monoclonal antibodies specific to tissue factor protein are generated using human B lymphocytes secreting antibody specific to tissue factor protein (see Human Hybridomas and Monoclonal Antibodies [eds. Engelman, E. G., Plenum Press, 1985]). These B lymphocytes could be generated by in vitro immunizations. Tissue factor specific lymphocytes are transformed by Epstein-Barr virus or fused to immortal human lymphoblastoid, human myeloma, human plasmacytomas or other immortal cell lines. The immortalized line secretes tissue factor specific human IgG. Human recombinant molecule preparation may also be produced by the methods claimed in EP Publication No. 0125023, published Nov. 14, 1984, which describes the combining of a variable region of a monoclonal antibody to the constant region of heavy or light chain of human antibodies.

EXAMPLE 3

Localization of Tissue Factor Biosynthesis

Normal Vessels

Figure 1B:
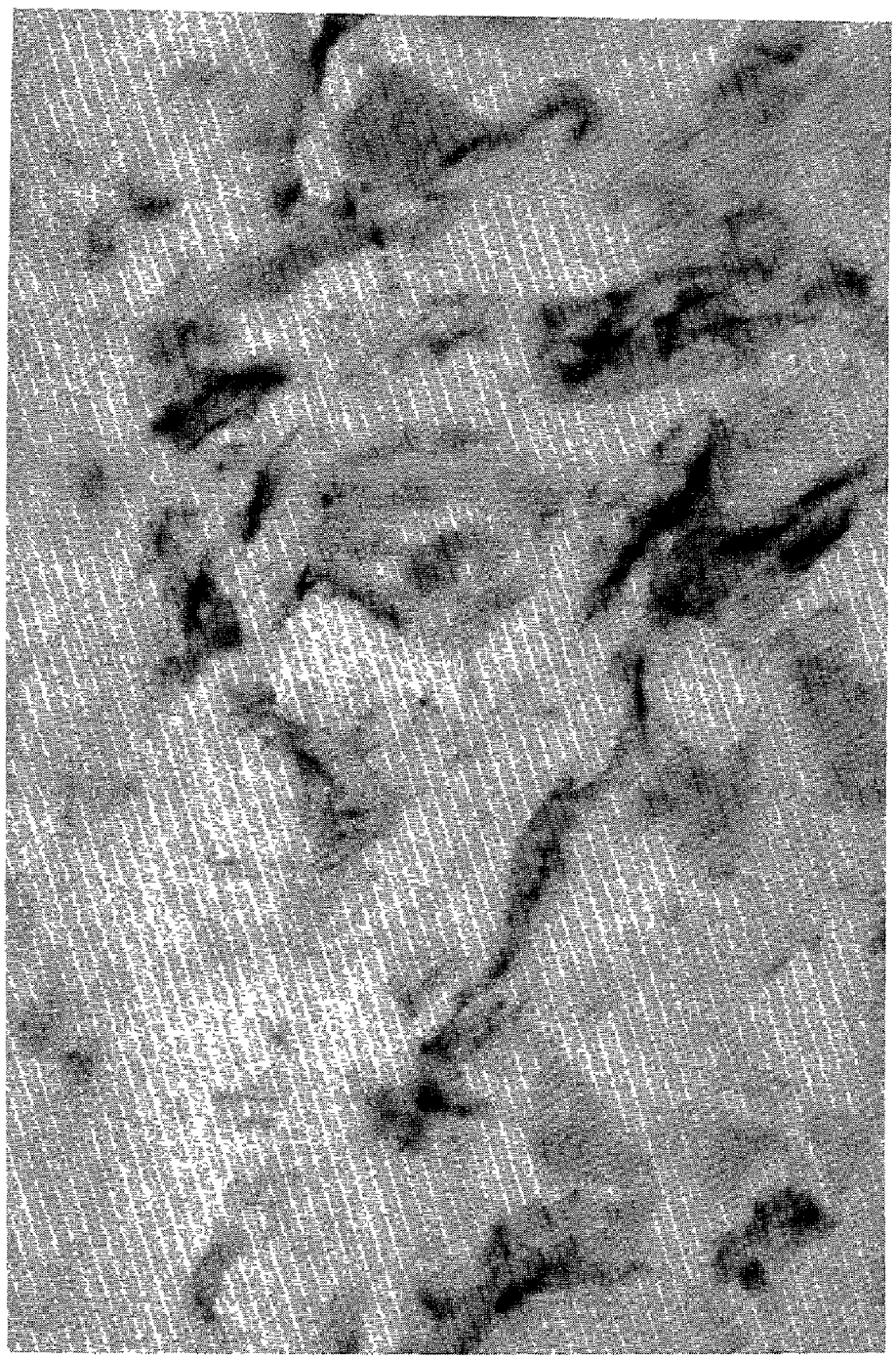
Figure 1C:
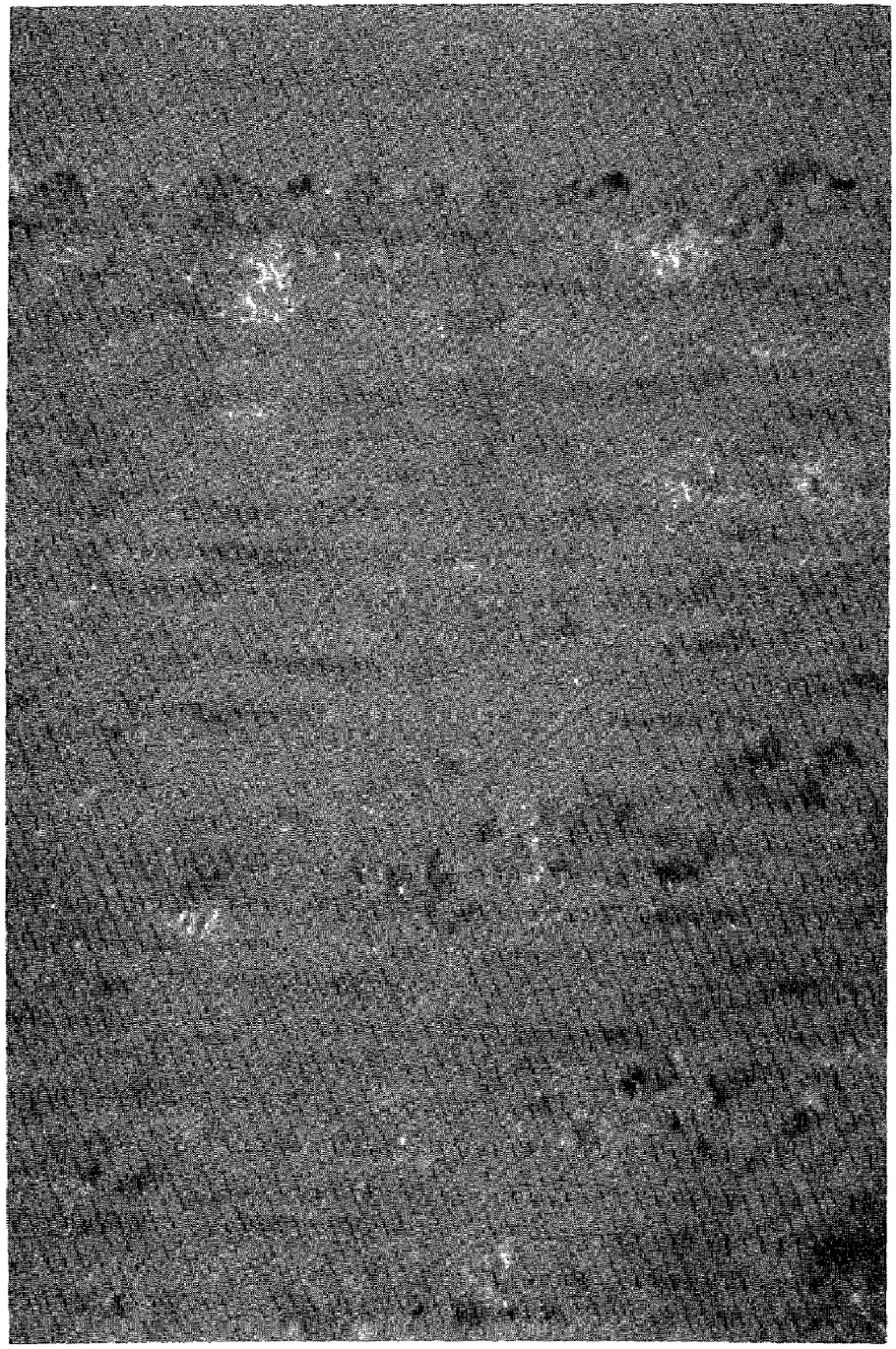

Normal human saphenous vein and internal mammary artery samples were examined for tissue factor biosynthesis. Endothelial cells were negative for tissue factor mRNA and protein (FIG. 1a). Tissue factor positive cells were found dispersed in the tunica media and in the adventitia adjacent to the vessel. The strongest labelling was seen over the adventitia where adventitial fibroblasts showed intense tissue factor staining (FIG. 1b) and mRNA hybridization. Scattered cells in the tunica media contained tissue factor mRNA as determined by in situ analysis (FIG. 1c). Immunochemical staining of the media, however, was unimpressive and fairly weak, but appeared to be cell associated and correlated well with the in situ results (FIG. 1a). In general, more cells were found to be positive in the media by in situ hybridization than could be detected by immunochemical staining. This may suggest reduced tissue factor translation or tissue factor secretion by these cells. Tissue factor positive cells in the media did not show typical smooth muscle cell morphology. The cytoplasm of these cells stained poorly with eosin, did not display a typical pancake shaped cytoplasm but rather appeared more cuboidal in shape and had small dense nuclei. Cells with this morphology typically do not stain with alpha smooth muscle actin antibodies (HHF35) and must be considered undefined.

The immunocytochemistry and in situ hybridization indicate that tissue factor is synthesized by smooth muscle cells in the tunica media and by fibroblasts in the adherent adventitia surrounding normal vessels. There was no evidence of tissue factor mRNA or protein localization in endothelial cells of any vessel studied. Previous cell culture work had suggested that induction of tissue factor synthesis by the endothelial cells represents a major procoagulant mechanism by which endothelial cells participate in homeostasis (Bevilacqua, Am. J. Pathol. 121:393–403 [1985]), and vascular smooth muscle cells have been shown to produce tissue factor at much higher levels (Maynard, J. Clin. Invest. 55:814–824 [1975]). Induction of endothelial tissue factor biosynthesis may be a normal mechanism by which the endothelium modifies homeostasis or alternatively be a response of the endothelium to infection and endotoxin stimulation.

Atherosclerotic Plaques

Figure 2A:
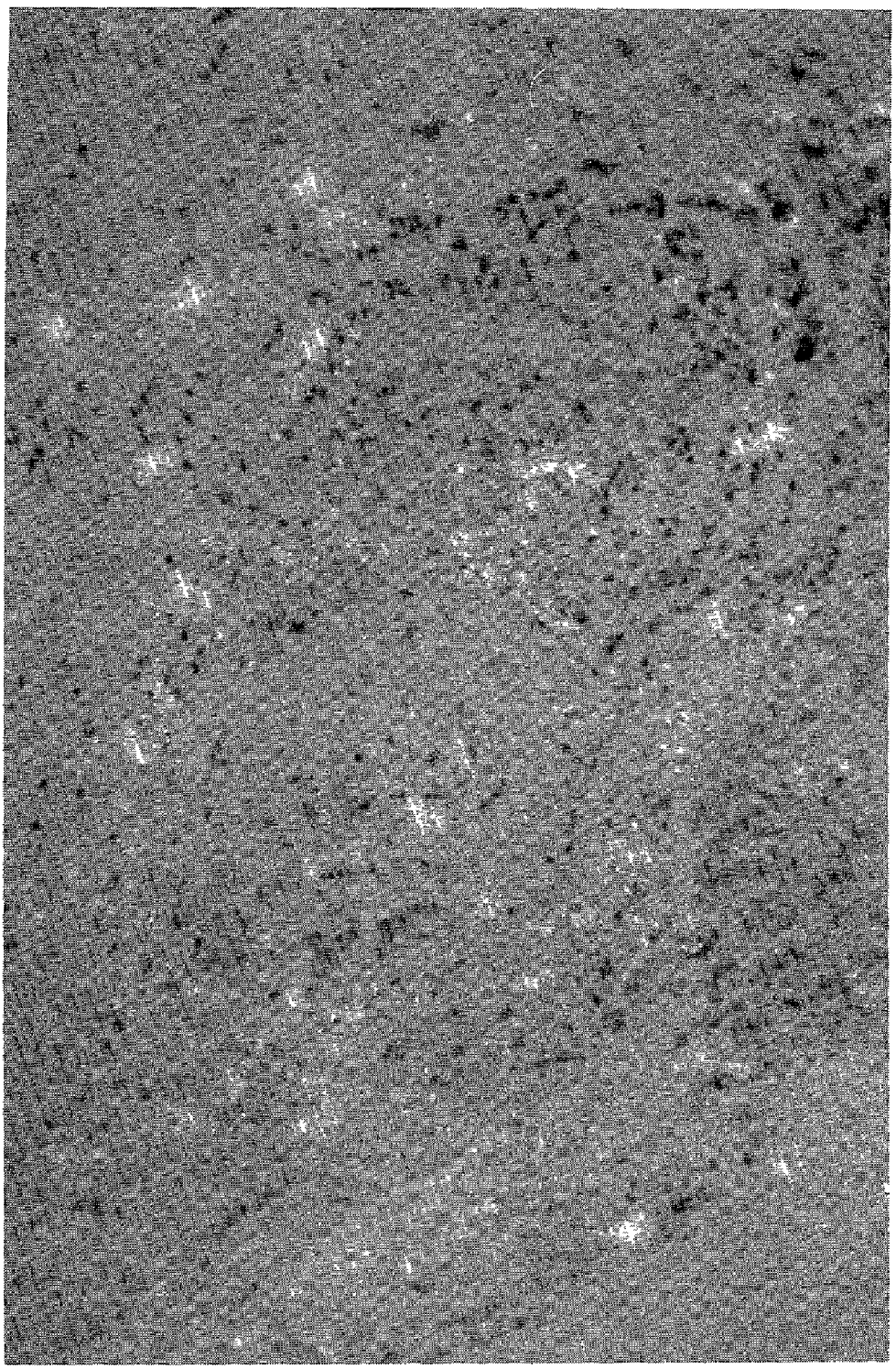
FIGS. 2a–c (herein referred to as FIG. 2). Localization of tissue factor in the human atherosclerotic plaque by in situ hybridization and immunohistochemistry. Carotid endarterectomy specimens were hybridized to an $^{35}$S-labelled tissue factor mRNA probe (panel A, magnification 125×) and revealed many cells producing tissue factor in the atherosclerotic plaque. Immunohistochemistry with tissue factor antibody RD010 indicated strong staining of the necrotic core region of the plaque particularly in areas adjacent to the cholesterol clefts that was not entirely cell associated (panel B, magnification 125×). In situ hybridization of serial sections indicated that there were cells containing tissue factor mRNA adjacent to the cholesterol clefts (panel C, magnification 310×) suggesting local synthesis of the tissue factor protein detected in this region.

Human atherosclerotic plaques obtained from carotid endarterectomy surgery were examined for tissue factor mRNA and protein using the above techniques. Extensive mRNA hybridizations were seen in several regions of atherosclerotic plaque (FIG. 2a). Positive cells were found scattered throughout the fibrous cap, the base and shoulder region of the plaque as well as in the necrotic core adjacent to the cholesterol clefts (FIG. 2c). The normal media underlying the endarterectomy specimens did not contain any tissue factor or mRNA positive cells. Six plaques were screened and cells showing positive hybridization were seen in all of them.

Figure 2B:
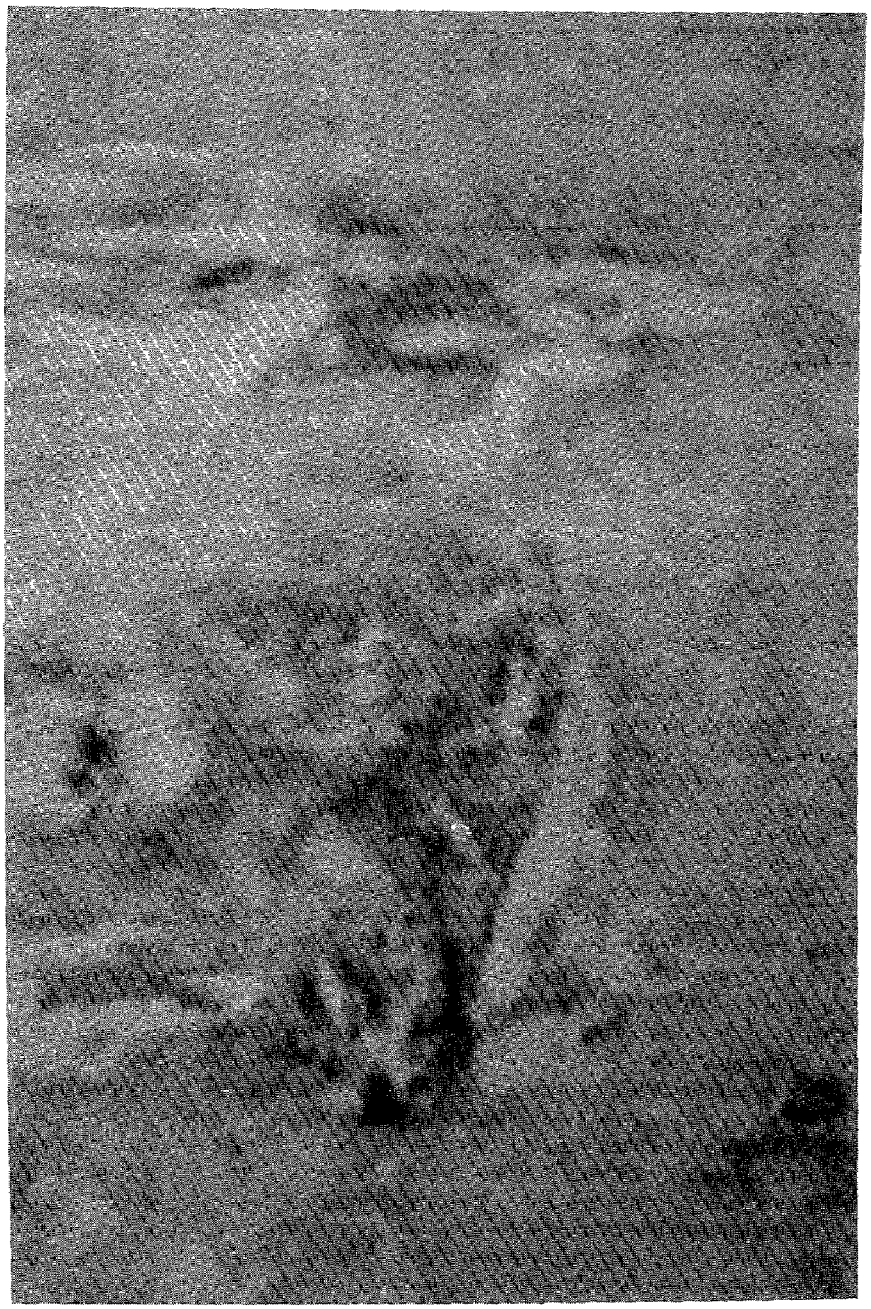
Figure 2C:
Figure 3A:
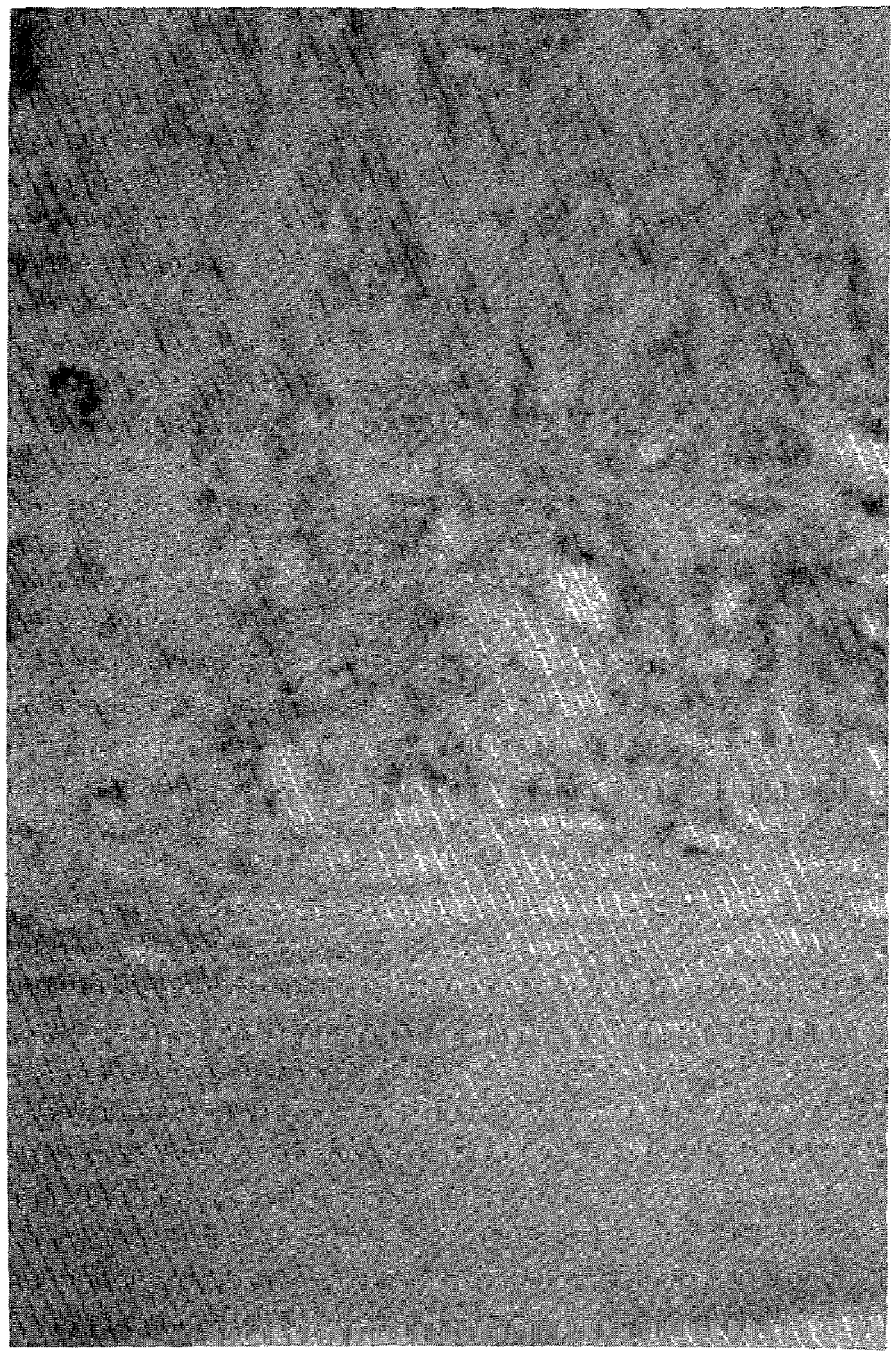
FIGS. 3a–b (herein referred to as FIG. 3). Localization of tissue factor protein in macrophage foam cell regions of the atherosclerotic plaque by immunohistochemistry (panel A, magnification 125×; panel B, magnification 500×).
Figure 3B:
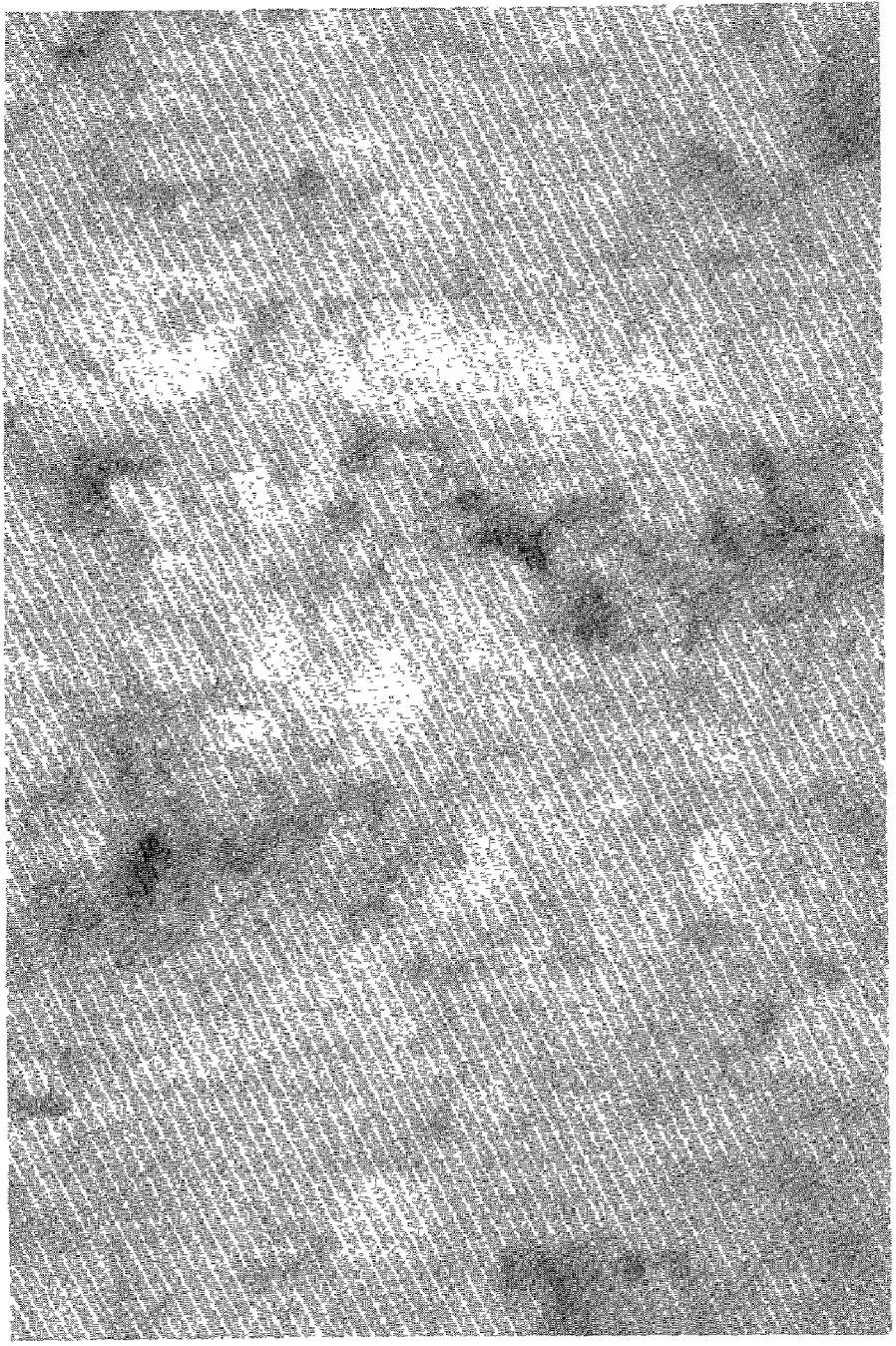

The necrotic cores of the plaques were characterized by extensive tissue factor protein localization in the extracellular matrix particularly surrounding cholesterol clefts (FIG. 2b). Additional protein staining was also seen in the macrophage-rich foam cell regions of atherosclerotic plaques (FIG. 3). Such foam cell-rich regions often lay underneath the fibrous cap and adjacent to the necrotic cores. Finally, as with the normal vessels, no tissue factor mRNA or protein was detected in surface or capillary endothelium. Of 18 endarterectomy specimens screened, only one sample was negative for TF immunostaining, ten showed localization to foam cells, six to the necrotic core and eight to mesenchymal appearing cells. It was possible to confirm that the protein staining and the in situ hybridization labelled the same cells on serial sections. This observation served as a control for both the immunohistochemistry and hybridization analysis. Additional controls were run on serial sections in every experiment. The in situ hybridizations were controlled by hybridization of serial sections with PDGF-A chain or PDGF receptor specific cRNA probes (Wilcox, et al.,J. Clin. Res., 82, 1988). Different patterns of hybridization were seen with these probes compared to tissue factor. Tissue factor immunohistochemistry was always controlled by incubation of serial sections with pre-immune serum that failed to label any cells at all.

Atherosclerotic plaques were found to have significantly more tissue factor protein compared to normal saphenous veins, internal mammary artery, or regions of normal media underlying the plaque. Tissue factor protein mRNA was found in both mesenchymal like intimal cells in the atherosclerotic intima as well as in macrophages and cells adjacent to the cholesterol clefts which appear to be macrophages as well. Immunocytochemistry indicated that there is a considerable amount of tissue factor protein trapped in the extracellular matrix of the necrotic core of the atherosclerotic plaque. This is not cell associated but is locally synthesized since cells adjacent to these regions contain tissue factor mRNA. Tissue factor protein found in the necrotic core may be shed from the cell surface of the synthetic cells (Bona, R. et al., Thromb. Res., 48: 487–500 [1987]) and subsequently trapped in the surrounding lipid matrix. Alternatively, the tissue factor protein in this region may originate from cells that have died and left tissue factor rich membranes behind.

The immunostaining of macrophage foam cells suggests that in these cells tissue factor is intracellular as well as possibly cell surface associated. To what extent such stores of tissue factor are macrophage-derived or whether this protein originates from phagocytosis of surrounding necrotic core debris is not clear. Levy , J. Clin. Invest. 67:1614–1622 (1981) have shown that certain lipoprotein fractions can induce procoagulant activity originating from monocytes/macrophages. The production of tissue factor by macrophages has been demonstrated by other investigators (Tipping, Am. J. Pathol. 131:206–212 [1988]; Levy, supra). In addition, we have shown macrophages with tissue factor mRNA. Tissue factor represents the final common pathway for both the intrinsic and extrinsic pathways of coagulation (Nemerson, Y., Blood 71:1–8 [1988]). It is a highly thrombogenic peptide and requires only phospholipid and factor VII/VIIa to activate factor X directly and indirectly via factor IX activation, leading to the generation of thrombin. Factor VII is normally present in blood but requires binding to tissue factor for activation of factor X (Nemerson, Y., supra). Since there is no in vivo coagulation in the absence of vascular damage it is reasonable to assume that tissue factor would not normally be exposed to blood (Nemerson, supra; Spicer, PNAS [USA] 84:5148–5152 [1987]). This is consistent with our findings since normal vessel endothelial cells in direct contact with the blood do not synthesize or store tissue factor. Since tissue factor is found in scattered smooth muscle cells in the tunica media and adventitial cells adherent to the vessel, vessel wall rupture into these areas would be required to expose the blood to significant stores of procoagulant tissue factor activity. Zaugg et al., J. Clin. Chem. and Clin. Biochem. 18:545 (1980) have shown that damaged human aorta exposes factor VII dependent procoagulant activity in support of this hypothesis.

EXAMPLE 4

Tissue Factor Coagulation Assays

Functional tissue factor activity was demonstrated in human atherosclerotic plaque by incubating plaque fragments with factors X and VII in the presence of calcium. The generation of Xa in that system was measured by its ability to induce clotting in human factor XII-deficient plasma. In the absence of plaque, no measurable Xa-activity was generated (FIG. 4, control). Addition of increasing amounts of plaque reduced the clotting time proportionally: 40.3±3.8 mg (n=3 plaques) gave a clotting time of 112±17.2 sec., whereas 81.1 mg±12.3 mg (n=3 plaques) of plaque gave a clotting time of 73±19 sec. Plaques could be rinsed in a buffer and reused at least 4 times without loss of tissue factor activity. This procoagulant activity could be inhibited by preincubation of the tissue with the affinity purified tissue factor neutralizing antibody RD010, described above, (4.9 $\mu$g in an incubation volume of 75 $\mu$L prolonged clotting time to 431±9.1 sec. with 40±3.8 mg of plaque tissue) (See FIG. 4). Complete reversal of procoagulant activity with increasing concentrations of antibody could not be achieved. These results indicate that the tissue factor protein detected in the plaque by immunohistochemistry is active and may participate in the initiation of coagulation if released or exposed in vivo.

Advanced human atherosclerosis is characterized by intimal smooth muscle cell proliferation accompanied by accumulation of fats and inflammatory cells including macrophages and T cells within the atherosclerotic plaque (Ross, N. Eng. J. Med. 314:488–500 [1986]; Gown et al., Am. J. Pathol. 125:191–207 [1986]; Jonasson, L., Arteriosclerosis 6:131–138 [1986]). Thrombosis is commonly the critical event which converts an asymptomatic atherosclerotic plaque into a symptomatic one (Falk, Br. Heart J. 50:127–134 [1983]; Sherman, N. Eng. J. Med. 315:913–919 [1986]) whereas non-diseased arteries hardly ever become thrombosed. Plaque rupture is likely to be an integral event that precipitates clot formation (Forrester, Circulation 75:505–513 [1987]). An occlusive mural thrombus accompanies most cases of acute myocardial infarctions (Buja, L. M., Am. J. Cardiol. 47:343–356 [1981]). Plaque rupture or cracking is normally found to underlie such thrombi, and in many cases the thrombus is seen to extend into the region of the necrotic core of the plaque extruding through such cracks. This is true of both the coronary (Falk, Br. Heart J. 50:127–134 [1983]; Chapman,I., Arch. Pathol. 80:256–261 [1965]; Drury, J. Path. Bact. 67:207–215 [1954]) and cerebral arteries (Constantinides, Arch. Pathol. 83;422–428 [1967]). The source of the thrombogenicity of the plaque had not previously been determined but these results indicate that a thrombus results when blood components come into contact with the tissue factor protein present within the plaque. The results show that there is a) significant synthesis of tissue factor protein in atherosclerotic plaques; b) that tissue factor protein accumulates in the necrotic core and is found in foam cell rich regions of the plaque; and c) that there is in the plaque procoagulant activity due to tissue factor protein as identified by in vitro coagulation assays that is significantly reduced by tissue factor protein antagonists. The overproduction and trapping of tissue factor protein in the atherosclerotic plaque may play a role in thrombosis and reocclusion of an atherosclerotic vessel following thrombolytic therapy.

EXAMPLE 5

Test for Coronary Artery Thrombosis

Mongrel dogs or rabbits weighing approximately 20–25 kg or 2–4 kg, respectively, are anesthetized with a slow intravenous injection of sodium pentobarbital, incubated and placed on an artificial ventilator. A left thoracotomy is performed in the 5th–6th intercostal space, and an arterial catheter is placed in the internal mammary artery for blood pressure monitoring. Procainamide (1.5 g injected intramuscularly in 2–3 sites) is then provided, the pericardium is opened, and a pericardial cradle is prepared. The left anterior descending coronary artery is dissected out from the epicardium, side branches are ligated, and a 2.5 cm segment is isolated. An electromagnetic flow probe (Carolina Medical Electronics FM501, King, N.C.) is placed on the most proximal portion of the segment and intravenous lidocaine (15 mg bolus followed by a constant infusion at 1 mg/min) is infused. A control left coronary angiogram is performed by injecting approximately 2 ml of Renograffin 76, by hand, through a modified Judkin's 7 French catheter inserted from a carotid artery. 1 ml of blood is then removed and kept in a syringe for later use in forming the thrombus, and heparin (5000 U intravenous bolus) is administered. Additional 1000 U boluses of heparin are administered at hourly intervals. A permanent 2 mm wide constrictor is placed near the distal end of the segment and adjusted so as to reduce coronary artery blood flow to approximately 40±10% of control.

High resolution post-mortem angiograms in selected animals show that a constriction, so placed, decreases the luminal diameter by more than 90%. The 1 cm of coronary artery just proximal to the constriction is then emptied of blood and isolated between temporary silk snares. Intimal damage is induced by grasping the segment with forceps, and then the segment is flushed by releasing the proximal snare and injection of saline retrograde through a cannulated side branch. The segment is then reisolated and 0.2 ml of thrombin (Parke-Davis topical thrombin, 1000 U/ml, Morris Plains, N.J.) is introduced. 0.1 ml of the stored blood is injected into this isolated segment. After approximately 5 minutes, first the proximal and then the distal ties are released and the side branch catheter is removed. During this procedure, the permanent constrictor remained in place.

Approximately 30 minutes after injecting the thrombin and blood, and after a repeated angiogram confirms the presence of a complete coronary artery occlusion, slow intravenous injections of tissue factor protein antagonists, acetylsalicylic acid (35 mg/kg) or dipyridamole (0.6 mg/kg) are administered. Approximately 10 minutes later, a 30-minute infusion of rt-PA (15 μg/kg/min for the two chain form or 30 μg/kg/min for the single chain form) is initiated.

If partial coronary artery reperfusion does not occur within the 30-minute infusion period, rt-PA infusion is continued for an additional 30 minutes. The blood flow in the affected vessel is monitored continuously. An angiogram is immediately performed after restoration of blood flow. The reperfusion time is taken as the number of minutes from the beginning of the rt-PA infusion until reperfusion is documented by the flow meter and is confirmed by the repeat angiogram showing complete antegrade filling of the artery with rapid clearance of the dye (less than 4 cardiac cycles). After reperfusion is obtained, blood flow is monitored for evidence of reocclusion, with a final confirmation again being obtained by angiography, using the same criteria as are used for establishing reperfusion. The reocclusion time is taken as the interval between documented reperfusion and reocclusion. The above described animal model closely simulates the response to thrombolytic therapy by human patients having acute myocardial infarction.

Bleeding times are performed before and 30 min after injections of the tissue factor protein antagonists with a spring-loaded blade device (Simplate, General Diagnostic, Morris Plains, N.J. or Surgicutt Int. Technidyne Corp., Edison, N.J.), applied to a shaved foreleg. Venous blood samples for determination of the levels of fibrinogen, activated partial thromboplastin time, ADP-induced platelet aggregation are collected into 0.01 M citrate containing 150 KIU/ml aprotinin. (Sigma, St. Louis, Mo.) Platelet counts are performed on blood drawn into EDTA using an automated particle counter (Coulter, Hialeah, Fla.).

EXAMPLE 6

Comparison of Thrombolytic Potency and Effect on Reocclusion of Bolus Injections of rt-PA and rt-PA plus Tissue Factor Protein Antagonists The thrombolytic potency and effect on reocclusion of bolus injections of rt-PA alone is compared to that of combined injections of rt-PA and tissue factor protein antagonist using the animal model of Example 5.

Bolus injections of 450 μg/kg of rt-PA at 15 min intervals is given (with high grade [over 90%] superimposed stenosis).

Injection of about 0.01 to 25.0 mg/kg of tissue factor protein antagonist is followed 10 min later by a single bolus injection of 450 μg/kg of rt-PA in dogs to test for reperfusion within 5–10 min without reocclusion during an observation period of 2 hours.

EXAMPLE 7

Inverted Arterial Graft

Rabbits were anesthetized with pentobarbital. The femoral artery was dissected out and a 4–7 cm segment isolated by hemostat clamps. An electromagnetic flow probe (Carolina Medical Electronics, King, N.C.) was placed on the most proximal portion of the segment. The femoral artery segment was then removed, inverted and sutured back in place. The clamps were then removed and blood flow restored. Normally there was total occlusion (measured as cessation of blood flow) of the inverted arterial segment by a platelet rich thrombus within minutes of the release of the hemostat clamps. Various treatments including injection of tissue factor protein antagonists alone or in combination with tPA and/or inhibitors of platelet aggregation were evaluated by the time to arterial occlusion measured by the flow meter. Postmortem pathology included examination of the inverted arterial segment by scanning electron microscopy (SEM) to determine extent of platelet deposition.

Bleeding times were measured before and thirty minutes after injections of the tissue factor protein antagonists with a spring-loaded blade device applied to the ear. Venous blood samples were taken for determination of the levels of fibrinogen, activated partial thromboplastin time and ADP-induced platelet aggregation. Platelet counts were performed on blood drawn into EDTA using an automated particle counter.

Rabbits were prepared as described and injected with 150 U/kg heparin i.v. and 3 mg/kg tissue factor protein antagonist D3 (a monoclonal antibody described in Example 1) injected i.v. ten minutes prior to release of the hemostat clamps. An additional 9 mg/kg of the tissue factor antagonist was injected via the superficial epigastric artery subsequent to clamp release. Three animals out of three did not occlude after thirty minutes, whereas control animals treated with heparin alone occluded within the first ten minutes.

What is claimed is:

1. A method of treating a coagulation disorder in a patient having an atherslcrotic plaque comprising administering to the patient a therapeutically effective amount of lipoprotein associated coagulation inhibitor ("LACI").

2. The method according to claim 1, further comprising administering a thrombolytic agent to the patient.

3. The method according to claim 2, wherein The thrombolytic agent is selected from the group consisting of a streptokinase. urokinase, prourokinase and a tissue-type plasminogen activator.

4. The method according to claim 2, wherein the LACI is given at a dose in the range of 0.01–25.0 mg per kg of patient weight and the thrombolytic agent is given at a dose in the range of 0.01–2.5 mg per kg of patient weight.

5. The method according to claim 1 wherein The administration is by bolus.

6. The method according to claim 1 wherein the administration is by intravenous infusion.

7. The method according to claim 1 wherein the patient is a human.

* * * * *